United States Patent
Joffre et al.

(10) Patent No.: US 8,877,216 B2
(45) Date of Patent: *Nov. 4, 2014

(54) COSMETIC AND SKIN-CARE COMPOSITIONS COMPRISING SACCHARIDE-SILOXANE COPOLYMERS

(75) Inventors: Eric Jude Joffre, Midland, MI (US); Bethany K. Johnson, Midland, MI (US); Brian Jeffery Swanton, Saginaw, MI (US); Michael Stephen Starch, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 540 days.

This patent is subject to a terminal disclaimer.

(21) Appl. No.: 11/915,051

(22) PCT Filed: May 23, 2006

(86) PCT No.: PCT/US2006/020210
§ 371 (c)(1),
(2), (4) Date: Mar. 26, 2008

(87) PCT Pub. No.: WO2006/127883
PCT Pub. Date: Nov. 30, 2006

(65) Prior Publication Data
US 2008/0199417 A1    Aug. 21, 2008

Related U.S. Application Data

(60) Provisional application No. 60/683,590, filed on May 23, 2005.

(51) Int. Cl.
| | |
|---|---|
| *A61Q 19/08* | (2006.01) |
| *A61Q 1/12* | (2006.01) |
| *A61Q 5/06* | (2006.01) |
| *A61Q 5/12* | (2006.01) |
| *A61K 8/89* | (2006.01) |
| *A61K 8/06* | (2006.01) |
| *A61K 8/893* | (2006.01) |
| *A61Q 19/00* | (2006.01) |
| *A61Q 1/02* | (2006.01) |
| *A61Q 15/00* | (2006.01) |

(52) U.S. Cl.
CPC ... *A61K 8/89* (2013.01); *A61Q 1/02* (2013.01); *A61K 2800/52* (2013.01); *A61Q 5/06* (2013.01); *A61K 8/06* (2013.01); *A61K 8/893* (2013.01); *A61Q 5/12* (2013.01); *A61Q 15/00* (2013.01); *A61Q 19/00* (2013.01)
USPC ........ 424/401; 424/69; 424/70.12; 424/78.08

(58) Field of Classification Search
None
See application file for complete search history.

(56) References Cited

U.S. PATENT DOCUMENTS

| | | |
|---|---|---|
| 2,676,182 A | 4/1954 | Daudt et al. |
| 2,857,356 A | 10/1958 | Goodwin |
| 3,159,601 A | 12/1964 | Ashby |
| 3,220,972 A | 11/1965 | Lamoreaux |
| 3,296,291 A | 1/1967 | Chalk |
| 3,419,593 A | 12/1968 | Willing |
| 3,445,420 A | 5/1969 | Kookootsedes et al. |
| 3,516,946 A | 6/1970 | Modic et al. |
| 3,814,730 A | 6/1974 | Karstedt |
| 3,936,582 A | 2/1976 | Keiser |
| 3,989,667 A | 11/1976 | Lee et al. |
| 3,989,668 A | 11/1976 | Lee et al. |
| 4,263,274 A | 4/1981 | Kulkarni |
| 4,269,603 A | 5/1981 | Worth |
| 4,310,469 A | 1/1982 | Crivello |
| 4,313,988 A | 2/1982 | Koshar et al. |
| 4,370,358 A | 1/1983 | Hayes et al. |
| 4,447,562 A | 5/1984 | Ivani |
| 4,501,861 A | 2/1985 | Woodbrey |
| 4,558,110 A | 12/1985 | Lee |
| 4,584,355 A | 4/1986 | Blizzard |
| 4,584,361 A | 4/1986 | Janik |
| 4,585,836 A | 4/1986 | Homan |
| 4,591,622 A | 5/1986 | Blizzard |
| 4,591,652 A | 5/1986 | DePasquale et al. |
| 4,604,442 A | 8/1986 | Rich |
| 4,631,329 A | 12/1986 | Gornowicz |

(Continued)

FOREIGN PATENT DOCUMENTS

| | | |
|---|---|---|
| CA | 711756 | 6/1965 |
| DE | 19918627 | 10/2000 |

(Continued)

OTHER PUBLICATIONS

International Search Report corresponding to International Patent Application No. PCT/US2006/020210, European Patent Office, dated Feb. 22, 2007, 7 pages.

(Continued)

*Primary Examiner* — Jyothsna Venkat

(74) *Attorney, Agent, or Firm* — Nixon Peabody LLP

(57) ABSTRACT

A personal care composition comprising at least one saccharide-siloxane copolymer having a saccharide component and an organosiloxane component and linked by a linking group, wherein the saccharide-siloxane copolymer has a specified formula, is provided. The personal care composition is adapted to provide at least one benefit to the at least one portion of the body to which it is applied. Emulsions, methods for preparing emulsions comprising saccharide-siloxane copolymers, and personal care products comprising the personal care compositions and emulsions are also provided.

28 Claims, No Drawings

(56) References Cited

U.S. PATENT DOCUMENTS

| | | | |
|---|---|---|---|
| 4,707,531 A | 11/1987 | Shirahata | |
| 4,760,025 A | 7/1988 | Estell et al. | |
| 4,766,176 A | 8/1988 | Lee | |
| 4,774,281 A | 9/1988 | Chaffee et al. | |
| 4,784,879 A | 11/1988 | Lee et al. | |
| 4,793,555 A | 12/1988 | Lee et al. | |
| RE33,141 E | 1/1990 | Gornowicz et al. | |
| 4,939,128 A | 7/1990 | Kato et al. | |
| 4,962,076 A | 10/1990 | Chu et al. | |
| 4,999,437 A | 3/1991 | Dobler et al. | |
| 5,004,791 A | 4/1991 | Billmers | |
| 5,011,870 A | 4/1991 | Peterson | |
| 5,015,700 A | 5/1991 | Herzig et al. | |
| 5,017,654 A | 5/1991 | Togashi et al. | |
| 5,036,117 A | 7/1991 | Chung et al. | |
| 5,051,455 A | 9/1991 | Chu et al. | |
| 5,053,442 A | 10/1991 | Chu et al. | |
| 5,075,038 A | 12/1991 | Cole et al. | |
| 5,175,325 A | 12/1992 | Brown et al. | |
| 5,227,093 A | 7/1993 | Cole et al. | |
| 5,252,233 A | 10/1993 | Czech | |
| RE34,606 E | 5/1994 | Estell et al. | |
| 5,310,843 A | 5/1994 | Morita | |
| 5,352,724 A | 10/1994 | Fujiki et al. | |
| 5,380,527 A | 1/1995 | Legrow et al. | |
| 5,493,041 A | 2/1996 | Biggs et al. | |
| 5,626,660 A | 5/1997 | Lautenschlager et al. | |
| 5,654,362 A | 8/1997 | Schulz, Jr. et al. | |
| 5,665,155 A | 9/1997 | Hohner et al. | |
| 5,677,163 A | 10/1997 | Mainzer et al. | |
| 5,700,676 A | 12/1997 | Bott et al. | |
| 5,747,016 A * | 5/1998 | Yui et al. | 424/401 |
| 5,831,080 A | 11/1998 | Sejpka et al. | |
| 5,891,977 A | 4/1999 | Dietz et al. | |
| 5,895,794 A | 4/1999 | Berg et al. | |
| 5,972,682 A | 10/1999 | Bott et al. | |
| 5,981,680 A | 11/1999 | Petroff et al. | |
| 5,990,069 A | 11/1999 | Andre et al. | |
| 6,043,328 A | 3/2000 | Domschke et al. | |
| 6,051,216 A | 4/2000 | Barr et al. | |
| 6,066,326 A | 5/2000 | Afriat et al. | |
| 6,066,727 A | 5/2000 | Yamamoto et al. | |
| 6,132,822 A | 10/2000 | Overcash et al. | |
| 6,136,758 A | 10/2000 | Yamada et al. | |
| 6,218,560 B1 | 4/2001 | Abele et al. | |
| 6,221,979 B1 | 4/2001 | Lin et al. | |
| 6,239,194 B1 | 5/2001 | Standke et al. | |
| 6,255,429 B1 | 7/2001 | Griffin et al. | |
| 6,361,716 B1 | 3/2002 | Kleyer et al. | |
| 6,372,833 B1 | 4/2002 | Chen et al. | |
| 6,391,322 B1 | 5/2002 | Roulier et al. | |
| 6,398,911 B1 | 6/2002 | Schroeder et al. | |
| 6,414,139 B1 * | 7/2002 | Unger et al. | 556/413 |
| 6,433,055 B1 | 8/2002 | Kleyer et al. | |
| 6,436,382 B1 | 8/2002 | Chopra et al. | |
| 6,440,429 B1 | 8/2002 | Torizuka et al. | |
| 6,448,329 B1 | 9/2002 | Hirschi et al. | |
| 6,465,550 B1 | 10/2002 | Kleyer et al. | |
| 6,471,952 B1 | 10/2002 | Dubief et al. | |
| 6,471,985 B2 | 10/2002 | Guyuron et al. | |
| 6,485,716 B1 | 11/2002 | Fei et al. | |
| 6,500,883 B1 | 12/2002 | Mack et al. | |
| 6,506,444 B1 | 1/2003 | Mahr et al. | |
| 6,517,933 B1 | 2/2003 | Soane et al. | |
| 6,521,084 B1 | 2/2003 | Burger et al. | |
| 6,534,581 B1 | 3/2003 | Kleyer et al. | |
| 6,762,289 B1 | 7/2004 | O'Lenick, Jr. et al. | |
| 6,783,692 B2 | 8/2004 | Bhagwagar | |
| 6,791,839 B2 | 9/2004 | Bhagwagar | |
| 6,815,486 B2 | 11/2004 | Bhagwagar et al. | |
| 7,005,281 B2 | 2/2006 | Ohrlein et al. | |
| 7,074,490 B2 | 7/2006 | Feng et al. | |
| 7,199,205 B2 | 4/2007 | Okawa et al. | |
| 7,205,373 B2 | 4/2007 | Brandstadt et al. | |
| 7,208,561 B2 | 4/2007 | Yoshitake et al. | |
| 7,354,982 B2 | 4/2008 | Yoshitake et al. | |
| 7,649,087 B2 | 1/2010 | Yoshitake et al. | |
| 7,741,253 B2 | 6/2010 | Hanes | |
| 7,834,087 B2 | 11/2010 | Joffre et al. | |
| 7,871,987 B2 | 1/2011 | McSuliffe et al. | |
| 2001/0021387 A1 | 9/2001 | Krammer et al. | |
| 2001/0053897 A1 | 12/2001 | Frate et al. | |
| 2003/0202948 A1 * | 10/2003 | Koini et al. | 424/59 |
| 2004/0071746 A1 | 4/2004 | Popplewell et al. | |
| 2004/0077816 A1 | 4/2004 | Brandstadt et al. | |
| 2004/0082024 A1 | 4/2004 | Brandstadt et al. | |
| 2004/0091541 A1 | 5/2004 | Unger | |
| 2004/0091730 A1 | 5/2004 | Hart et al. | |
| 2004/0241130 A1 | 12/2004 | Tamareselvy et al. | |
| 2004/0247552 A1 | 12/2004 | Blin et al. | |
| 2004/0254275 A1 | 12/2004 | Fukui et al. | |
| 2005/0043365 A1 | 2/2005 | Yoshitake et al. | |
| 2006/0013791 A1 | 1/2006 | Shimizu et al. | |
| 2006/0216259 A1 | 9/2006 | Haubennestel | |
| 2008/0138386 A1 | 6/2008 | Joffre et al. | |
| 2008/0200612 A1 | 8/2008 | Joffre et al. | |
| 2008/0209645 A1 | 9/2008 | Carrillo et al. | |
| 2009/0169501 A1 | 7/2009 | Feng et al. | |
| 2009/0258058 A1 | 10/2009 | Thomas et al. | |
| 2010/0105582 A1 | 4/2010 | Joffre et al. | |

FOREIGN PATENT DOCUMENTS

| | | |
|---|---|---|
| EP | 0180377 | 5/1986 |
| EP | 0300525 | 1/1989 |
| EP | 0363252 | 4/1990 |
| EP | 0438496 | 7/1991 |
| EP | 0444921 | 9/1991 |
| EP | 0465744 | 1/1992 |
| EP | 0506241 | 9/1992 |
| EP | 0572416 | 9/1992 |
| EP | 0347895 | 11/1993 |
| EP | 0698633 | 2/1996 |
| EP | 0562922 | 5/1997 |
| EP | 0848029 | 6/1998 |
| EP | 0865787 | 9/1998 |
| EP | 0869142 | 10/1998 |
| EP | 0874017 | 10/1998 |
| EP | 0934959 | 8/1999 |
| EP | 0962482 | 12/1999 |
| EP | 1020494 | 2/2000 |
| EP | 1057872 | 12/2000 |
| EP | 1201817 | 5/2002 |
| EP | 1331248 | 7/2007 |
| GB | 2407496 | 5/2005 |
| JP | 62-68820 | 4/1987 |
| JP | 63 139106 | 6/1988 |
| JP | 03-290127 | 12/1991 |
| JP | 61-096593 | 12/1992 |
| JP | 5-186596 | 7/1993 |
| JP | 5-331291 | 12/1993 |
| JP | 7-041414 | 2/1995 |
| JP | 7-041415 | 2/1995 |
| JP | 7-041416 | 2/1995 |
| JP | 7-041417 | 2/1995 |
| JP | 7-070204 | 3/1995 |
| JP | 07-133352 | 5/1995 |
| JP | 8-134103 | 5/1996 |
| JP | 8-269204 | 10/1996 |
| JP | 9-136901 | 5/1997 |
| JP | 09-202714 | 8/1997 |
| JP | 10-029910 | 2/1998 |
| JP | 10-029915 | 2/1998 |
| JP | 10-029921 | 2/1998 |
| JP | 10-298288 | 11/1998 |
| JP | 11-092490 | 4/1999 |
| JP | 11-106310 | 4/1999 |
| JP | 10-512000 | 11/1999 |
| JP | 11-343347 | 12/1999 |
| JP | 11-349450 | 12/1999 |
| JP | 11-349601 | 12/1999 |
| JP | 2002-146025 | 5/2002 |
| JP | 2006-290837 | 10/2006 |
| JP | 2009-057380 | 3/2009 |

(56) References Cited

FOREIGN PATENT DOCUMENTS

| WO | WO 90-03809 | 4/1990 |
|---|---|---|
| WO | WO 92-14428 | 9/1992 |
| WO | WO 94-29322 | 12/1994 |
| WO | WO 94-29324 | 12/1994 |
| WO | WO 96-15309 | 5/1996 |
| WO | WO 96-18729 | 6/1996 |
| WO | WO 98-49998 | 11/1998 |
| WO | WO 98-50006 | 11/1998 |
| WO | WO 99-55953 | 11/1999 |
| WO | WO 00-78844 | 12/2000 |
| WO | WO 01-25385 | 4/2001 |
| WO | WO 01-96450 | 12/2001 |
| WO | WO 02-41709 | 5/2002 |
| WO | WO 02-088456 | 11/2002 |
| WO | WO 03-020770 | 3/2003 |
| WO | WO 03-042283 | 5/2003 |
| WO | WO 03-050144 | 6/2003 |
| WO | WO 2004-016626 | 2/2004 |
| WO | WO 2004-108175 | 12/2004 |
| WO | WO 2005-047378 | 5/2005 |
| WO | WO 2005-063855 | 7/2005 |
| WO | WO 2006-025552 | 3/2006 |
| WO | WO 2006-064928 | 6/2006 |
| WO | WO 2006-065282 | 6/2006 |
| WO | WO 2006-066227 | 6/2006 |
| WO | WO 2006-071772 | 7/2006 |
| WO | WO 2006-107003 | 10/2006 |
| WO | WO 2006-107004 | 10/2006 |
| WO | WO 2006-127883 | 11/2006 |
| WO | WO 2007-139812 | 12/2007 |
| WO | WO 2008-046763 | 4/2008 |
| WO | WO 2008-103219 | 8/2008 |
| WO | WO 2009-019144 | 2/2009 |
| WO | WO 2009-052272 | 4/2009 |
| WO | WO 2009-079610 | 6/2009 |
| WO | WO 2009-125126 | 10/2009 |
| WO | WO 2009-150846 | 12/2009 |

OTHER PUBLICATIONS

Written Opinion of the International Searching Authority corresponding to International Patent Application No. PCT/US2006/020210, European Patent Office, dated Nov. 23, 2007, 11 pages.

Muraoka, et al. "Hair preparations containing organopolysiloxanes having sugar substituents," XP002402424, Database accession No. 1989: 179250; Chemical Abstracts Service, Columbus, Ohio, US; May 12, 1989.

Akimoto, T. et al. Macromol. Chem. Phys. 2000, 201, 2729-2734.

Database WPI Derwent Publications Ltd., London, GB; AN 1988-201757 (XP002395828).

Gupta et al. Biotechnol. Appl. Biochem. (2003) 37: 63-71.

Wagner et al. "Silicon-Modified Carbohydrates Surfactants III: Cationic and Anionic Compounds" Applied Organometallic Chemistry (1997) vol. 11, pp. 523-538.

Simionescu, Bogdan C., Valeria Harabagiu and Cristofor I. Simionescu, "Siloxane-Containing Polymers" in The Polymeric Materials Encyclopedia, CRC Press, Inc., 1996.

Hardman, Bruce, Arnold Torkelson, "Silicones" in Encyclopedia of Polymer Science and Engineering, Edited by H.F. Mark, et.al., 1989, p. 243, vol. 15.

Pearson et al., *Handbook of Reagents for Organic Synthesis, Activating Agents and Protecting Groups*, © 1999 John Wiley & Sons Ltd., West Sussex, PO19 1UD, UK, pp. 102, 205, 416, 417.

Lindhorst, *Essentials of Carbohydrate Chemistry and Biochemistry*, Second Revised and Updated Edition, © 2003 Wiley-VCH Verlag GmbH & Co., KGaA, Weinheim, pp. 39-78.

* cited by examiner

COSMETIC AND SKIN-CARE COMPOSITIONS COMPRISING SACCHARIDE-SILOXANE COPOLYMERS

CROSS-REFERENCE TO RELATED APPLICATION

This application is a nationalization of PCT/US2005/020210 filed on May 23, 2006, which claims benefit to U.S. Provisional Application No. 60/683,590, filed on May 23, 2005.

The present invention relates to personal care compositions comprising saccharide-siloxane copolymers, and personal care products formed therefrom. The copolymers comprise a hydroxyl functional saccharide component and an organosiloxane component. The saccharide may be covalently bound to the organosiloxane at one or more pendant or terminal positions, or some combination thereof, through linkages including but not limited to ether, ester, and amide bonds. Personal care products formulated from the personal care compositions provide enhanced performance benefits.

Saccharide-functional silicones, and processes for making them, are known in the art. For example, U.S. Pat. No. 4,591,652 describes methods for manufacturing polyhyroxyl silanes by reacting silanes having amine-terminated substituents with aldonic acid lactones. Japanese Patent No. 62-68820 discloses organopolysiloxanes comprising saccharide residues made from aminosiloxanes and saccharide lactones. WO 94/29324 describes siloxanyl-modified compounds, methods for their preparation and applications as surface-active and surface-modifying agents, particularly in the plant protection art. It more particularly discloses surface-active or surface-modifying agents formed from epoxy-trisiloxane reaction products and saccharide lactones. WO 02/088456 describes amido-functional aminopolydiorganosiloxanes, processes for the production thereof, preparations comprising the amido-functional aminopolydiorganosiloxanes and uses in the textile industry. The amido-functional siloxanes are formed from reacting aminosiloxanes and saccharide lactones.

Synthetic processes for linking saccharides and siloxanes are also known. For example, U.S. Pat. No. 5,831,080 describes organosilicone compounds containing glycoside radicals made by hydrosilylating allyl functional saccharide groups. U.S. Pat. No. 6,517,933 B1 describes a hybrid polymer material comprising a set of naturally occurring building blocks which include saccharides, and a set of synthetic building blocks which include polysiloxanes. A number of potential linking chemistries are described.

The above referenced patent art describes saccharide-functional siloxane copolymers which may be suitably used in the practice of embodiments of the present invention. The patents are fully incorporated herein by reference. A person of ordinary skill in the art will readily appreciate, however, that a large variety of saccharide-siloxane copolymers may be similarly employed.

Silicone-based ingredients, including organosiloxanes, are commonly recognized in the personal care industry for their ability to confer desirable properties to skin and hair care compositions, which then provide enhanced benefits to the body target substrate. Such benefits include the provision of, inter alia, enhanced skin feel, spreadability and application, control of greasiness, and absorption into the substrate. In addition, certain saccharide ingredients are known in the industry to provide beneficial effects to skin care products and are frequently added to personal care compositions. For example, gluconic acid in the form of gluconolactone is currently contained in some skin care products, and galactose has been employed in anti-wrinkle creams. Lactobionic acid (4-O—B-D-galactopyranosyl-D-gluconic acid), a known tissue-damage suppressant and anti-oxidant with a polyhydroxy acid structure is currently a popular benefit agent added to some cosmetic preparations.

Many personal care compositions include ingredients which do not directly benefit the personal care target substrate, but are necessary to provide particular rheological or other chemical and/or mechanical properties to the applied product. Many of these ingredients result in secondary, incidental, unintended, and often undesirable effects including, for example, increases in tackiness or propensity for residue formation, and decreases in consumer perception of desirable sensory or manageability attributes. It would be advantageous to provide an agent which confers enhanced personal care performance benefits while decreasing the need for additives that provide mostly formulation benefits and which may even detract from the personal care performance of the composition as a whole. In addition, in today's cultural climate there is decreased discretionary time and a consumer desire to spend less time attending to personal care needs. Hence, there is an increase in the demand for personal care formulations which confer multiple benefits in a single product or a single product application. This results in the necessity of combining ingredients into product formulations in order to provide separate benefits contemporaneously, and the increase in the occurrence of combining ingredients that antagonize one another with respect to, for example, the efficacy of those benefits. Consumers are continually seeking personal care products providing improved performance benefits while minimizing undesirable characteristics incidental to that performance, and consumers are continually seeking personal care products that allow more efficient use without sacrificing desired performance benefits.

Thus, there is a continuing need in the personal care industry for formulations which impart enhancements to the qualities typically found desirable in such applications as hair care, skin care, antiperspirants and cosmetics. Further, there is a continual need for products which provide these enhancements with a minimum need for supportive, potentially performance-detracting additives, and there is a continual need for products which provide desired performance in a way that is time-efficient to the consumer.

The present invention is based on the surprising discovery that compositions comprising saccharide-siloxane copolymers confer enhanced performance benefits to a wide variety of personal care products. These benefits are realized both indirectly, through permitting a decrease in excipient product formulation ingredients that do not benefit a target substrate, and directly, through providing enhanced sensory and conditioning benefits directly to the target substrate. In addition, formulating personal care products with the personal care compositions surprisingly provides a synergistic effect with respect to certain benefits which conventionally derive from ingredients which antagonize one another. Accordingly, embodiments of the present invention provide personal care compositions, personal care products, and methods of treating personal target substrates such as hair and skin.

Accordingly, one embodiment of the present invention provides a personal care composition. The personal care composition comprises: (i) at least one saccharide-siloxane copolymer. The saccharide-siloxane copolymer has a saccharide component and an organosiloxane component which are linked by a linking group. The saccharide-siloxane copolymer has the following formula:

$$R^2_a R^1_{(3-a)} SiO-[(SiR^2R^1O)_m-(SiR^1_2O)_n]_y-SiR^1_{(3-a)}R^2_a$$

wherein each $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each a is independently 0, 1, 2, or 3, y is an integer such that the copolymer has a molecular weight less than 1 million, $R^2$ has the formula Z-$(G^1)_b$-$(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:
$R^3$—NHC(O)—$R^4$—;
$R^3$—NHC(O)O—$R^4$—;
$R^3$—NH—C(O)—NH—$R^4$—;
$R^3$—C(O)—O—$R^4$—;
$R^3$—O—$R^4$—;
$R^3$—CH(OH)—CH$_2$—O—$R^4$—;
$R^3$—S—$R^4$
$R^3$—CH(OH)—CH$_2$—NH—$R^4$—; and
$R^3$—N($R^1$)—$R^4$, and $R^3$ and $R^4$ are divalent spacer groups comprising $(R^5)_r(R^6)_s(R^7)_t$, where at least one of r, s and t must be 1, and $R^5$ and $R^7$ are either $C_1$-$C_{12}$ alkyl or $((C_1$-$C_{12})O)_p$ where p is any integer 1-50 and each $(C_1$-$C_{12})O$ may be the same or different, $R^6$ is —N($R^8$)—, where $R^8$ is H or $C_1$-$C_{12}$ alkyl, or is Z—X where Z is previously defined or $R^3$, X is a carboxylic acid, phosphate, sulfate, sulfonate or quaternary ammonium radical, and at least one of $R^3$ and $R^4$ must be present in the linking group and may be the same or different, and wherein the saccharide-siloxane copolymer is a reaction product of a functionalized organosiloxane polymer and at least one hydroxy-functional saccharide such that the organosiloxane component is covalently linked via the linking group, Z, to the saccharide component.

The personal care composition is further adapted to provide at least one benefit to the at least one portion of the body to which it is applied. The personal care composition also optionally comprises (ii) a carrier medium suitable to permit topical application of the personal care composition to at least one portion of the body. In addition the composition may optionally comprise (iii) a cross-linker which acts to cross-link among the saccharide-siloxane copolymers and/or with the substrates.

In specific embodiments the saccharide-siloxane copolymer is solubilized in a suitable solvent or solvent blend and then formed into dispersions in the form of emulsions or solutions for ease of delivery into the personal care compositions.

An additional embodiment is directed to an emulsion comprising an internal phase which comprises at least one of the saccharide-siloxane copolymers as formulaically disclosed above. In this embodiment the dispersion of the internal phase is maintained by a surfactant and the continuous phase is water. The emulsion may be further diluted with water to provide a concentration of actives suitable for a particular personal care application.

A further embodiment provides methods for preparing the emulsions. Various degrees of agitation may be employed to achieve emulsions with properties desirable for particularly intended applications. In an even more specific embodiment, emulsion polymerization is employed whereby the saccharide-siloxane monomers are polymerized into higher molecular weight polymers within each micelle of the emulsion.

Another embodiment is directed to personal care products comprising the personal care compositions. Specific personal care product embodiments are directed to shampoos, rinse-off and leave-in conditioners, cleansers, hair relaxants, stylants, colorants, antiperspirants, moisturizers, color cosmetics, including facial foundations and cover-ups. Embodiments of the personal care products are provided in forms including rinses, lotions, creams, gels, mousses, ointments, sprays, aerosols, soaps, moisturizers, solids, solid sticks, soft solids, or solid gels.

Method embodiments are also provided including specific method embodiments for treating hair and skin, and methods for styling and holding hair. The methods comprise administering a safe and effective amount of a personal care product comprising the personal care compositions.

The personal care compositions will comprise additional actives and excipients according to the type of personal care product intended to be formulated therefrom. Persons of ordinary skill in the personal care formulation art will appreciate the wide variety of agents available which are necessary or desirable for particular applications.

These and other aspects and advantages of the present invention will become apparent from the following detailed description of the preferred embodiments.

Saccharide-siloxane copolymers were surprisingly found to impart enhanced benefits to personal care compositions formulated therefrom. The copolymers possess unique properties such as increased hydrogen bonding and surface activity that in turn confer unique characteristics to the personal care compositions comprising them. As used herein, the art of "personal care" is intended to include any topical treatment of any portion of the body that is intended to provide at least one benefit to that portion of the body. The at least one benefit may be direct or indirect, and may be sensory, mechanical, cosmetic, protective, preventative or therapeutic. While it is contemplated that the human body is a particularly desirable target substrate for the presently disclosed personal care compositions and products formulated therefrom, it will be readily apparent to one skilled in the art that other mammals having similar tissues, especially keratinacious tissue such as skin and hair, may be suitable target substrates and that therefore veterinary applications are within the scope of the present invention.

The novel personal care compositions, as provided, are adapted to provide at least one benefit to at least one portion of the body. As used herein, "adapted" means formulated in a manner that permits safe and effective application of the at least one benefit to the at least one portion of the body. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

A person of ordinary skill in the personal care formulation arts will appreciate the well-known criterion for selecting the essential ingredients, optional additives and excipients, that are suitable according to the intended application of a particular personal care composition. Non-limiting examples of additives which may be formulated into the personal care compositions in addition to the saccharide-siloxane copolymer include: additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, anti-dandruff, anti-acne, anti-carie and wound healing-promotion agents.

It is not uncommon for certain benefits to be sacrificed in personal care products formulated to provide multiple benefits in a single product. For instance, with respect to hair, an increase in conditioning benefit is often accompanied by a decrease in hair "body" or volume. Addition of the saccharide-siloxane copolymer permits the formulation of products which combine such benefits without sacrificing the efficacy of some, and, indeed, in some formulations it provides synergy with respect to the combination of benefits. Personal care products formulated from the personal care compositions comprising the saccharide siloxane copolymer surprisingly provide enhancements in benefits which typically derive from effects which antagonize one another, for example, enhancing both conditioning and curl retention benefits. They also surprisingly provide thickening benefits in hair, skin, AP and color cosmetics.

In addition, the inclusion of the saccharide-siloxane ingredient to personal care compositions may eliminate or lessen the need for certain other excipient additives. For example, because of the increased hydrogen bonding properties of the saccharide-siloxane copolymers, they are effective thickening agents for cyclic silicones such as cyclomethicone and lessen the need for other thickening additives which may incidentally confer undesirable product properties such as stringency, residue formation and/or conditioning defects.

The saccharide-siloxane copolymer component of the personal care composition typically exists as gums, waxy solids or solids at ambient conditions. It should be noted, however, that there is a small subset of the copolymer that does exist in a liquid form, and liquid dispersible forms may also be produced by manipulating conditions such as temperature. However, in order for most of the saccharide-siloxane copolymers to achieve a viscosity range that permits ready formation of dispersions, for example solutions or emulsions, they must first be solubilized by being dissolved in a suitable solvent or solvent blend.

The solubilized copolymer is then used to form a solution or emulsion for ready delivery into the personal care composition. The particular solvent blend is selected based upon the ionic properties of the saccharide-siloxane copolymer, and the suitability of that solvent for the intended application. In one specific embodiment the solvent blend comprises a mixture of paraffin and an alcohol. In a very specific embodiment the alcohol comprises isopropyl alcohol.

The term "dispersion" as used herein means a two-phase system where a first phase comprises finally divided particles distributed throughout a bulk second phase and the first phase constitutes an "internal" or dispersed phase while the second phase constitutes an "external" or continuous phase.

The term "solution" as used herein is intended broadly to include mechanical dispersions, colloidal dispersions and true solutions, and should not be construed as limited to the latter. A solution is a dispersion comprising a uniformly dispersed mixture wherein a first phase constitutes the solute and a second phase constitutes the solvent.

The term "emulsion" as used herein means a dispersion comprising a mixture of two immiscible liquids with the liquid constituting the first, dispersed internal phase being suspended in the second, continuous phase with the aid of an emulsifier.

One embodiment is directed to a personal care composition. The personal care composition comprises (i) at least one saccharide-siloxane copolymer having a saccharide component and an organosiloxane component and linked by a linking group. The saccharide-siloxane copolymer has the following formula:

$$R^2_a R^1_{(3-a)}SiO-[(SiR^2R^1O)_m-(SiR^1_2O)_n]_y-SiR^1_{(3-a)}R^2_a$$

wherein each $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each a is independently 0, 1, 2, or 3, y is an integer such that the copolymer has a molecular weight less than 1 million, $R^2$ has the formula $Z-(G^1)_b-(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:

$R^3$—NHC(O)—$R^4$—;
$R^3$—NHC(O)O—$R^4$—;
$R^3$—NH—C(O)—NH—$R^4$—;
—$R^3$—C(O)—O—$R^4$—;
—$R^3$—O—$R^4$—;
$R^3$—CH(OH)—$CH_2$—O—$R^4$—;
$R^3$—S—$R^4$
$R^3$—CH(OH)—$CH_2$—NH—$R^4$—; and
$R^3$—N($R^1$)—$R^4$, and $R^3$ and $R^4$ are divalent spacer groups comprising $(R^5)_r(R^6)_s(R^7)_t$, where at least one of r, s and t must be 1, and $R^5$ and $R^7$ are either $C_1$-$C_{12}$ alkyl or $((C_1$-$C_{12})O)_p$ where p is any integer 1-50 and each $(C_1$-$C_{12})O$ may be the same or different, $R^6$ is —$N(R^8)$—, where $R^8$ is H or $C_1$-$C_{12}$ alkyl, or is Z—X where Z is previously defined or $R^3$, X is a carboxylic acid, phosphate, sulfate, sulfonate or quaternary ammonium radical, and at least one of $R^3$ and $R^4$ must be present in the linking group and may be the same or different, and wherein the saccharide-siloxane copolymer is a reaction product of a functionalized organosiloxane polymer and at least one hydroxy-functional saccharide such that the organosiloxane component is covalently linked via the linking group, Z, to the saccharide component.

The personal care composition is adapted to provide at least one benefit to the at least one portion of the body to which it is applied. The personal care composition further optionally comprises: (ii) a carrier medium suitable to permit topical application of the personal care composition to at least one portion of the body. In addition, the composition may optionally comprise (iii) a cross-linker which acts to cross-link among the saccharide-siloxane copolymers and/or with the substrates.

Cross-linkers suitable for use in practicing the present invention are well known in the art. In specific embodiments the crosslinking substantially occurs between the hydroxy-functional groups of the saccharide components. In more specific embodiments the cross-linker may be selected from the following non-limiting examples: boric acid, borate ester (e.g. tri-n-propyl borate, triisopropanolamine borate), alkyl boronic acid or ester (e.g. phenyl boronic acid), titanate, (e.g. titanium isopropoxide, diisopropoxytitanium bis(acetylacetonate)), zirconate, glyoxal, gluteraldehyde, epichlorohydrin, urea-formaldehyde, zirconium ammonium carbonate, salt of a multivalent ion, bifunctional epoxy or glycidyl compounds (e.g. 1,4 butanediol diglycidyl ether), di-(N-hydroxymethyl) urea, di-isocyanate (e.g. toluene diisocyante, hexamethylene diisocyanate), 2-chloro N,N di-ethylacetamide, sodium trimetaphosphate, phosphorous oxychloride, acrolein, N-methyl urea, dicarboxylic acid, bis-acid chloride, dialkyldichlorosilane (e.g. dimethyldichlorosilane), alkyltrichlorosilane (e.g. Methyltrichlorosilane), reactive siloxane resin, and combinations thereof. In a very specific embodiment, the cross-linker comprises a reactive siloxane resin or boronic acid or ester.

In a more specific embodiment the saccharide-siloxane copolymer is delivered to the personal care composition as a dispersion. Diluting or dispersing the copolymers makes them easier to process and suitably employable solvents include polydimethylsiloxanes, hydrocarbons, and alcohols. Particularly suitable solvents are cyclic siloxanes and hydrocarbon-alcohol mixtures and water.

Due to the compatibility of the saccharide-siloxane copolymer with hydrocarbons, silicones and alcohols, as well as with water, they may be incorporated into both aqueous and non-aqueous based personal care products which provide benefits to the at least one portion of the body. In embodiments where the portion of the body comprises hair, the benefit may include increased ease and hold of hair-styling, fixative effects and shine-enhancement.

Various synthetic routes to suitable saccharide siloxane copolymers are well known in the art and may be employed. One of ordinary skill in the art will appreciate that suitable saccharide-siloxanes may be formed from a variety of synthetic means and that the saccharide may be covalently linked to the siloxane through a variety of linking bonds including esters, ethers, amides, urethanes, ureas, epoxides and the like.

In one embodiment of the personal care composition at least one of the hydroxyl-functional saccharides comprises an aldonic acid or an oligoaldonic acid. In a more specific embodiment the aldonic acid or the oligoaldonic acid comprises a lactone.

Two exemplary lactones include gluconolactone (GL) and lactobionolactone (LBL). Both gluconolactone (GL) and lactobionolactone (LBL) are commercially available. Gluconic acid, found naturally occurring in cells, is a polyhydroxy alpha-hydroxy aldonic acid known to provide beneficial effects to skin and hair. It is typically contained in products marketed as personal care products in the gluconolactone form. Lactobionic acid (4-O-beta-D-galactopyranosyl-D-gluconic acid) is comprised of a galactose molecule attached to one molecule of gluconic acid via an ether-like linkage. Galactose is a chemically neutral, endogenous hexose sugar utilized in glycosaminoglycan synthesis, collagen synthesis, and wound-healing applications. Lactobionic acid is formed by oxidation of the disaccharide lactose (milk sugar) and a major commercial application is in the organ transplant art as a constituent of organ preservation fluid. Without being bound by theory, it is believed that this function relates to its ability to suppress tissue damage caused by oxygen radicals and is mediated through inhibition of hydroxyl radical production via complexation of Fe II. In the last decade work emerged suggesting particular efficacy in the personal care industry, specifically in products directed to skin care and anti-aging formulations. While GL and LBL are readily commercially available saccharides, one of ordinary skill in the art will appreciate that other saccharides are suitable for forming the copolymers of the present invention.

In specific embodiments of the personal care composition, the organosiloxane polymer comprises a polydimethylsiloxane. In some embodiments the linking group comprises an amide, an amino, a urethane, a urea, an ester, an ether, a thioether, or an acetal functional linking group. In more specific embodiments the linking group comprises an amino functional linking group, and in very specific embodiments the amino functional linking group comprises aminopropyl or aminoethylaminoisobutyl functional groups.

Aldonolactones are particularly suitable saccharides when the organosiloxane comprises amino-functionality and in very specific embodiments the saccharide-siloxane copolymer comprises the reaction product of an amino-functional organosiloxane and a lactone. Hence, in even more specific embodiments, the saccharide-siloxane copolymer comprises the reaction product of an amino-functional organosiloxane and an aldonolactone such as GL or LBL.

The saccharide-siloxane copolymers may be formulated into the personal care compositions in a substantially pure form, or as dispersions in the form of either solutions or emulsions. Depending on the form used, the saccharide-siloxane copolymers may be formulated into oil in water, water in oil, water in silicone and silicone in water systems. In the case of some aqueous-based formulations the saccharide-siloxane may be added directly to the formulation as a solid. In one embodiment of the personal care composition the dispersion is in the form of a solution. The solvent may be substantially aqueous or substantially non-aqueous depending on the nature of the particular saccharide-siloxane selected. In a specific embodiment the substantially nonaqueous solvent comprises a volatile or non-volatile solvent and in a very specific embodiment the substantially nonaqueous solvent comprises a volatile hydrocarbon or a silicone or mixtures thereof. In a more specific embodiment the substantially nonaqueous solvent comprises a silicone.

The term "volatile" as used herein means that the solvent exhibits a significant vapor pressure at ambient conditions. Examples of suitable volatile silicones include siloxanes such as phenyl pentamethyl disiloxane, phenylethylpenamethyl disiloxane, hexamethyldisiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane and mixtures thereof. Particularly suitable silicones are the cyclomethicones. In a very specific embodiment the volatile silicone comprises a cyclic siloxane.

Since the saccharide-siloxane copolymer ingredient is typically added to the personal care composition formulations as a dispersion, one may describe its concentration with respect to either the dispersion component or the personal care composition as a whole. In one embodiment wherein the personal care composition comprises a dispersion, the dispersion comprises from about 0.1% to about 50% saccharide-siloxane by weight percent and from about 0.01% to about 25% saccharide-siloxane by weight percent of the composition. In a more specific embodiment the dispersion comprises from about 2% to about 40% saccharide-siloxane by weight percent and from about 0.2% to about 10% saccharide-siloxane by weight percent of the composition. In an even more specific embodiment the solution comprises about 20% saccharide-siloxane by weight percent and about 0.5 to about 2% saccharide siloxane by weight of the composition.

In one embodiment of the personal care composition, the dispersion is in the form of an emulsion. The emulsion additionally comprises at least one surfactant to maintain the dispersion, and water as the continuous phase. The internal phase comprises the dispersed solubilized saccharide-siloxane copolymer. Nonionic, amphoteric (including zwitterionic), anionic or cationic surfactants may all be suitable. Oil in water emulsions are typically used because they are easier to handle and disperse readily into water-based formulations.

An additional embodiment of the present invention is directed to a saccharide-siloxane emulsion. The emulsion is an oil in water emulsion comprising an internal phase comprising the saccharide-siloxane and a continuous phase comprising water. The saccharide-siloxane emulsion comprises at least one surfactant which maintains the dispersion of the internal phase due to its amphipathic character.

Other embodiments provide methods for preparing the emulsions. The saccharide-siloxane emulsions may be prepared either by: 1) emulsifying preformed saccharide-siloxane fluids and polymers or 2) by polymerizing saccharide-siloxane monomers into higher molecular weight fluids and polymers in each individual emulsion particle e.g. via emulsion or suspension polymerization. In one embodiment, a surfactant-water blend is added to a solubilized saccharide-siloxane copolymer first in order to establish the dispersion and fix the water phase. Optional additional portions of water are added as required by the desired property profile of the emulsion and/or its intended applications.

It will be understood by one of ordinary skill in the art that there is a continuum for the ease with which a desired emulsion forms. Saccharide-siloxane emulsions share similar constraints with other emulsions. That is, they are thermodynamically unstable, require a surfactant to maintain the dispersion, and need an input of energy to initiate emulsification. Simple agitation via mixing may be sufficient, or higher shear means including the employment of high shear devices may be required. In other instances, a polymer emulsification or inversion method is needed.

A degree of agitation necessary to form the emulsion may require employment of mixing devices. Mixing devices typically provide the required energy input. Non-limiting examples of these mixing devices spanning the shear range include: 1) a vessel with an impeller, for example, propeller, pitched blade impeller, straight blade impeller, Rushton impeller, or Cowles blade; 2) kneading type mixers, for example, Baker-Perkins; 3) high shear devices which use positive displacement through an orifice to generate shear, for example, homogenizer, sonolater, or microfluidizer; 4) high shear devices using a rotor and stator configuration, for example, colloid mills, homomic line mills, IKA, or Bematek; 5) continuous compounders with single or dual screws; 6) change can mixers with internal impellers or rotor/stator devices, for example, Turello mixer; and 7) centrifugal mixers, for example, Hauschild speedmixers. Combinations of mixing devices can also provide benefits, for example a vessel with an impeller can be connected to a high shear device.

The choice of mixing device is based on the type of internal phase to be emulsified. For example, low viscosity internal phases can be emulsified using high shear devices which use positive displacement through an orifice. However, in the case of high viscosity internal phases, a rotor/stator device, twin screw compounder or change can mixer are often better choices. In addition, internal phases that contain hydrophilic groups are often easier to emulsify and therefore a simple vessel configured with an impeller may be sufficient.

The viscosity of the saccharide-siloxane copolymers is dependent on such factors as the molecular weight of the siloxane portion, the number of saccharide units, the mole percent of saccharide units per siloxane, and external conditions such as temperature and pressure. One skilled in the art would recognize that variable internal phase viscosities may be achieved by varying proportions in blends of saccharide-siloxane copolymers with solvents or solvent mixtures.

The most desirable order of ingredient addition in the preparation of the emulsion is determined empirically. For example, a desirable order of addition for a thick-phase emulsification may be: (a) solubilize the saccharide-siloxane copolymer in a solvent or solvent blend to a desired viscosity; (b) blend in a surfactant; (c) add water in increments with shear until a thick phase emulsion forms; (d) dilute with water to desired concentration, with shear. A desirable order of addition for a "pre-mix" with high shear may be: (a) add all the water to a mixing vessel configured with an impeller; (b) blend at least one surfactant with the water; (c) slowly add the saccharide-siloxane copolymer phase to the water to make a rough emulsion; (d) convey the rough emulsion through a high shear device until a desired particle size is achieved.

Nonionic surfactants are suitable for making the emulsions and include alkyl ethoxylates, alcohol ethoxylates, alkylphenol ethoxylates, and mixtures thereof. Cationic, amphoteric and/or anionic surfactants are also suitable and are typically added in addition to a nonionic surfactant. In a specific embodiment the emulsion comprises at least one nonionic surfactant and in another specific embodiment the emulsion comprises at least one cationic surfactant and at least one nonionic surfactant.

In one embodiment of the personal care composition wherein the saccharide-siloxane is delivered to the composition in the form of an emulsion, the emulsion comprises from about 5% to about 95% saccharide-siloxane by weight percent of the emulsion and the composition comprises from about 0.01% to about 25% saccharide-siloxane by weight percent of the composition. In a more specific embodiment the emulsion comprises from about 10% to about 60% saccharide-siloxane by weight percent of the emulsion and from about 0.2% to about 10% saccharide-siloxane by weight percent of the composition. In an even more specific embodiment the solution comprises about 20-40% saccharide-siloxane by weight percent and about 0.5 to about 2% saccharide siloxane by weight of the composition.

The novel personal care compositions comprising the saccharide-siloxane copolymer may be formulated into personal care products. The personal care products may be functional with respect to the portion of the body to which they are applied, cosmetic, therapeutic, or some combination thereof. Conventional examples of such products include, but are not limited to: antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

In some personal care product embodiments comprising the personal care composition, inclusion of the saccharide-siloxane copolymer decreases the need for other thickening agents in the formulation. In these embodiments, desired viscosity or thickness of the product is maintained with a lesser amount than is typical of conventional thickeners. This is particularly desirable in products wherein the thickening agent antagonizes a desirable effect of another benefit agent, such as, for example, a conditioning agent. It is also desirable in products where one or more thickening agents are included for processing or formulation characteristics rather than for any desired benefit they provide to the portion of the body to which they are applied. In these cases the saccharide-siloxane copolymer ingredient may permit a decrease in the one or more thickening agents that possess antagonistic performance characteristics.

In some personal care product embodiments comprising the personal care composition, inclusion of the saccharide-siloxane copolymer decreases the need for water in oil, and more specifically water in silicone emulsifiers. The saccharide-siloxane copolymer itself provides emulsification properties. In these embodiments, desired emulsification of the product is maintained with a lesser amount than is typical of conventional water in silicone emulsifiers.

In a specific embodiment of the personal care product comprising the personal care composition, the at least one benefit comprises a conditioning benefit and the at least one portion of the body comprises hair. Specific examples of the conditioning benefit include, but are not limited to an antistatic, lubricity, shine, viscosity, tactile, manageability, or a styling benefit. Non-limiting examples of manageability benefits include ease of dry and/or wet combing. Non-limiting examples of styling benefits include curl retention or hair-relaxing benefits. The conditioner may be a rinse-off or leave-in conditioner. In a specific embodiment the conditioning benefit comprises a curl-retention benefit. In one aspect the personal care composition comprises at least one saccharide-siloxane wherein the linking group comprises an aminopropyl functional linking group.

Examples of suitable conditioning agents include, but are not limited to, cationic polymers, cationic surfactants, proteins, natural oils, silicones other than the saccharide-siloxanes, hydrocarbons, nonionic surfactants, amphoteric surfactants, or mixtures thereof. Examples of additional silicones which may be useful in the present personal care compositions include, but are not limited to: alkyl methyl siloxanes, amino siloxanes, cyclic siloxanes, gums, linear siloxanes, MQ siloxane resins, MTQ siloxane resins, and polyether siloxane copolymers.

Further embodiments of the present invention are direct to methods for providing at least one benefit to at least one portion of the body. One such method comprises administration of a safe and effective amount of a personal care product comprising the personal care composition to at least one portion of the body. In one specific embodiment, a method of treating hair comprising administering a safe and effective amount of the personal care composition is provided. A very specific embodiment provides a method of styling and holding hair comprising administering a safe and effective amount of the personal care composition. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

Formulating personal care products with the personal care composition comprising the saccharide-siloxane copolymer as described above provides a thickening benefit. In a specific embodiment, an antiperspirant, hair, skin and color cosmetic products are provided. The antiperspirant product is formulated with the personal care composition comprising the saccharide-siloxane copolymer as described above, wherein the at least one benefit comprises a thickening benefit sufficient to maintain suspension of antiperspirant salts when the formulation comprises a substantially less than typical amount of conventional thickeners. In specific embodiments, the antiperspirant product is provided in the form of a solid, a soft solid or a gel. In a more specific embodiment the solid form comprises a soft solid or a gel.

Another specific embodiment of the present invention is directed to an emulsification benefit for water in oil and more specifically, water in silicone formulations. Lower levels of typical water in silicone formulation aids are needed when the saccharide-siloxane copolymer is used in the formulation. In a more specific embodiment an antiperspirant product is formulated with the composition comprising the saccharide-siloxane copolymer. In an even more specific embodiment the solid form comprises a gel.

Another specific embodiment provides a personal care product comprising the personal care composition wherein the at least one benefit comprises an enhanced conditioning benefit and the at least one portion of the body comprises skin. An embodiment directed to a method of treating skin is provided which comprises: (1) administration of a safe and effective amount of the personal care product comprising the novel personal care composition; and (2) rubbing the safe and effective amount into the skin.

Another specific embodiment is directed to a color cosmetic product comprising the novel personal care composition wherein the at least one benefit comprises a cosmetic benefit. Mores specific embodiments are directed to liquid foundations.

The following examples further illustrate embodiments within the scope of the present invention. The examples are provided for illustrative purposes only and should not be construed as limiting the invention as defined by the claims. It will be apparent to one of ordinary skill in the art that many variations of the present invention are possible without departing from the spirit and scope disclosed herein.

EXAMPLES

The examples below provide methods for preparing the saccharide-siloxane copolymer ingredient in several delivery forms and the specific saccharide-siloxane copolymers synthesized thereby. Of course, it will be readily appreciated by a person of ordinary skill in the art that there are alternative methods of synthesis and a wide range of saccharide-siloxane copolymers which may be synthesized and suitably employed. Additional examples are directed to specific personal care product embodiments and are illustrative in nature.

The specificity of the exemplary embodiments is for convenience and should not be taken as limiting.

Example 1

Preparation of Suitable Saccharide-Siloxane Copolymers

This example illustrates saccharide-siloxane copolymers which may be suitably employed in the present personal care compositions, and syntheses thereof. The components of exemplary saccharide siloxanes suitable for practicing the present invention are disclosed in Table 1. Properties of exemplary suitable siloxanes are disclosed in Table 2.

TABLE 1

Saccharide-Siloxane Copolymer Descriptions

| Siloxane | Saccharide | Functionality:Saccharide | Solvent |
|---|---|---|---|
| A123 | GL | 1:1 | water |
| A21 | GL | 1:1 | heptane, cyclics |
| A32 | GL | 1:1 | heptane, cyclics |
| 8175 | GL | 1:1 | heptane, cyclics |
| 8211 | GL | 1:1 | heptane, cyclics |
| 8175/A12 | GL | 1:1 | dispersion in heptane, cyclics |
| A12 | LBL | 1:1 | dispersion in water |
| A21 | LBL | 1:1 | heptane, cyclics |
| A32 | LBL | 1:1 | heptane, cyclics |
| 8175 | LBL | 1:1 | heptane, cyclics |
| 8211 | LBL | 1:1 | heptane, cyclics |
| 8175/A12 | LBL | 1:1 | |

TABLE 2

Aminofunctional Polymers Employed

| polymer | cst | Mw | % NH$_2$ | DP theory | mpc F | functional group |
|---|---|---|---|---|---|---|
| DMS-A12 | 20-30 | 950 | 3.1 | 12 | | aminopropyl |
| DMS-A21 | 100-120 | 5000 | 0.65 | 66 | | aminopropyl |
| DMS-A32 | 2000 | 27000 | 0.085 | 363 | | aminopropyl |
| 2-8175 | 150-400 | 7800 | | 100 | 2.3 | isobutylethylenediamine |
| 2-8211 | 1000 | 23000 | | 300 | 1.9 | isobutylethylenediamine |

Abbreviations:
cst - Centistoke;
Mw - molecular weight;
DP - Degree of polymerization;
mpc F - mole percent functionality a) A12-GL DMS-A12 (Gelest Inc., Morrisville, Pa.), a 20-30 cst. telechelic polydimethylsiloxane endblocked with aminopropyl groups, is reacted with gluconolactone (GL)(Sigma-Aldrich, St. Louis, Mo.) at 1:1 amine:lactone stoichiometry in methanol at 50° C. Upon completion of the reaction, the methanol is removed with rotary evaporation. The resulting material is a solid.

b) A21-GL

DMS-A21 (Gelest Inc., Morrisville, Pa.), a 100-320 cst. telechelic polydimethylsiloxane endblocked with aminopropyl groups, is reacted with gluconolactone (GL)(Sigma-Aldrich, St. Louis, Mo.) at 1:1 amine:lactone stoichiometry in methanol at 50° C. Upon completion of the reaction, the methanol is removed with rotary evaporation. The resulting material is a wax-like solid.

c) A32-GL

DMS-A32 (Gelest Inc., Morrisville, Pa.), a 2000 cst. telechelic polydimethylsiloxane endblocked with aminopropyl groups, is reacted with gluconolactone (GL)(Sigma-Aldrich, St. Louis, Mo.) at 1:1 amine:lactone stoichiometry in methanol at 50° C. Upon completion of the reaction, the methanol is removed with rotary evaporation. The resulting material has a gum-like consistency d) 8175-GL DC® Q2-8175 Fluid (Dow Corning Corp., Midland, Mich.), a 150-400 cst. polydimethylsiloxane with pendant aminoethylaminoisobutyl groups (approximately 2.3 mole percent), is reacted with gluconolactone at 1:1 primary amine:lactone stoichiometry in methanol at 50° C. Upon completion of the reaction, the methanol is removed with rotary evaporation. The resulting material has a gum-like consistency.

e) 8211-GL

DC® 2-8211 Polymer (Dow Corning Corp., Midland, Mich.), a 1000 cst. polydimethylsiloxane with pendant aminoethylaminoisobutyl groups (approximately 1.9 mole percent), is reacted with gluconolactone at 1:1 primary amine:lactone stoichiometry in methanol at 50° C. Upon completion of the reaction, the methanol is removed with rotary evaporation. The resulting material has a gum-like consistency.

f) 8175/A12-GL

DC® Q2-8175 Fluid (Dow Corning Corp., Midland, Mich.), a 150-400 cst. polydimethylsiloxane with pendant aminoethylaminoisobutyl groups (approximately 2.3 mole percent), and DMS-A12 are mixed together in a 1:1 by weight solution. This mixture is reacted with GL at a 1:1 primary amine:lactone stoichiometry in methanol at 50° C. Upon completion of the reaction, the methanol is removed with rotary evaporation. The resulting material has is a wax-like substance.

g) A12-LBL

DMS-A12 (Gelest Inc., Morrisville, Pa.), a 20-30 cst. telechelic polydimethylsiloxane endblocked with aminopropyl groups, is reacted with lactobionolactone (LBL)(prepared from lactobionic acid, Sigma-Aldrich, St. Louis, Mo.) at 1:1 amine:lactone stoichiometry in methanol at 50° C. Upon completion of the reaction, the methanol is removed with rotary evaporation. The resulting material is a solid.

h) A21-LBL

DMS-A21 (Gelest Inc., Morrisville, Pa.), a 100-120 cst. telechelic polydimethylsiloxane endblocked with aminopropyl groups, is reacted with lactobiolactone (LBL)(prepared from lactobionic acid, Sigma-Aldrich, St. Louis, Mo.) at 1:1 amine:lactone stoichiometry in methanol at 50° C. Upon completion of the reaction, the methanol is removed with rotary evaporation. The resulting material is wax-like.

i) A32-LBL

DC® Q2-8175 Fluid (Dow Corning Corp., Midland, Mich.), a 150-400 cst. polydimethylsiloxane with pendant aminoethylaminoisobutyl groups (approximately 2.3 mole percent), is reacted with lactobionolactone (LBL) (prepared from lactobionic acid, Sigma-Aldrich, St. Louis Mo.) at 1:1 primary amine:lactone stoichiometry in methanol at 50° C. Upon completion of the reaction, the methanol is removed with rotary evaporation. The resulting material is wax-like.

j) 8175-LBL

DC® Q2-8175 Fluid (Dow Corning Corp., Midland, Mich.), a 150-400 cst. polydimethylsiloxane with pendant aminoehtylaminoisobutyl groups (approximately 2.3 mole percent), is reacted with lactobionolactone (LBL) (prepared from lactobionic acid, Sigma-Aldrich, St. Louis Mo.) at 1:1 primary amine:lactone stoichiometry in methanol at 50° C. Upon completion of the reaction, the methanol is removed with rotary evaporation. The resulting material is wax-like.

k) 8211-LBL

DC® 2-8211 Polymer (Dow Corning Corp., Midland, Mich.), a 1000 cst. polydimethylsiloxane with pendant aminoehtylaminoisobutyl groups (approximately 1.9 mole percent), is reacted with lactobionolactone (LBL) (prepared from lactobionic acid, Sigma-Aldrich, St. Louis Mo.) at 1:1 primary amine:lactone stoichiometry in methanol at 50° C. Upon completion of the reaction, the methanol is removed with rotary evaporation. The resulting material is a rubbery powder.

l) 8175/A12-LBL

DC® Q2-8175 Fluid (Dow Corning Corp., Midland, Mich.), a 150-400 cst. polydimethylsiloxane with pendant aminoehtylaminoisobutyl groups (approximately 2.3 mole percent), and DMS-A12 (Gelest Inc., Morrisville, Pa.), a 20-30 cst. telechelic polydimethylsiloxane endblocked with aminopropyl groups are mixed together in a 1:1 by weight solution. This mixture is reacted with LBL at 1:1 primary amine:lactone stoichiometry in methanol at 50° C. Upon completion of the reaction, the methanol is removed with rotary evaporation. The resulting material is wax-like.

Example 2

Preparation of Dispersions for Delivery of Saccharide-Siloxane Copolymer

This example illustrates dispersions, including solutions and emulsions, of the saccharide-siloxane copolymers prepared in Example 1. For each of the personal care application examples disclosed below, delivery of the saccharide-siloxane copolymer is accomplished by dispersing the solid form of the copolymer in a carrier medium for ease of incorporation into final formulations. Where "saccharide-siloxane" is referenced, the material is being incorporated as a solution comprising 20% saccharide-siloxane solid by weight percent, rather than in solid form. One exception, however, is the aqueous version of the rinse-off conditioner in which it is possible to incorporate the copolymer ingredient in either solid or dispersed form.

(i) Preparation of Solutions

An aqueous solution is made by adding saccharide-siloxane solid and water in the weight percentages shown in Table 3 into a closed container which is then rolled until the solids are fully dissolved (approximately 2-4 hours). For non-aqueous dispersions, the saccharide-siloxane solid is added with cyclopentasiloxane to a closed loop vessel and heated to 70° C. using a constant temperature bath. Periodic agitation is applied to the dispersion by any number of methods (e.g. use of a lightening mixer, dental mixer, or similar high-shear device, rolling, shaking, and so on). The length of time required for complete incorporation into solution varies from 2-10 hours depending on the solubility of the particular saccharide-siloxane.

As illustrated by the data in Table 4, saccharide-siloxanes (both the LBL and GL forms) prove to be effective thickeners for cyclic siloxanes. Table 4 also lists the viscosity of the thickened cyclic dispersions where it is able to be measured.

The saccharide-siloxane dilutions may also be incorporated into formulations in the form of an emulsion. Emulsions are frequently employed because they are easier to incorporate into water based formulations due to their lower viscosity and ease of handling.

In the examples listed below, the form of delivery for the saccharide-siloxane will be as a dispersion (meaning that the saccharide-siloxane is initially dispersed in either water or cyclopentasiloxane depending on solubility) or as an emulsion where the saccharide-siloxane is dispersed in water and stabilized with surfactants as described above. Where the dispersion form is introduced, cyclopentasiloxane will appear in the personal care formulation. This is delivered with the saccharide-siloxane and not as a separate addition for the case of these examples unless otherwise specified.

TABLE 3

Saccharide-siloxane Copolymer Dispersions

| Copolymer | Weight % Saccharide Siloxane | Weight % 245 Fluid | Weight % Water |
|---|---|---|---|
| a. A12-GL | 20.0 |  | 80.0 |
| b. A12 LBL | 20.0 |  | 80.0 |
| c. A21-GL | 20.0 | 80.0 |  |
| d. A21-LBL | 20.0 | 80.0 |  |
| e. A32-GL | 20.0 | 80.0 |  |
| f. 8175-GL | 20.0 | 80.0 |  |
| g. 8175-LBL | 20.0 | 80.0 |  |
| h. 8211 GL | 20.0 | 80.0 |  |
| i. 8211 LBL | 20.0 | 80.0 |  |

TABLE 4

Physical Form of 20% Saccharide-Siloxane Dispersions

| Dispersion Containing Saccharide-Siloxane | GL | LBL |
|---|---|---|
| A12 | Swollen Gel Particles | Opaque, Low Viscosity (30 cP) Fluid |
| A21 | Opaque, High Viscosity (100 P) Fluid | Translucent, High Viscosity Gum |
| A32 | Clear, High Viscosity (300 P) Fluid | Clear, High Viscosity Gum |
| 8175 | Clear, Medium Viscosity (50 P) Fluid | Translucent, High Viscosity Gum |
| 8211 | Clear, High Viscosity Gum | Swollen Gel Particles |

(ii) Preparation of Emulsions j. 8175-GL-GTMAC Cationic Sugar Siloxane Emulsion W/Nonionic Surfactant 8175-GL is diluted to 50% copolymer in 2-propanol. 194 g of this solution is loaded into a nitrogen purged, three-necked 500 mL round bottomed flask equipped with a condenser and temperature control and magnetic stirrer. 5.91 g of (2,3-epoxypropyl)-trimethylammonium chloride (Fluka, Buchs, Switerland) is added with stirring. The reaction is maintained at 50° C. for four hours. 50 g of a this solution is placed on a rotary evaporator and the solvent is removed until an 80% solid solution remains. 22 g of this solution, 0.9 g of Tergitol 15-S-3 and 2.6 g of Tergitol 15-S-40 nonionic surfactants are placed in a disposable cup and mixed on a centrifugal mixer (Hauschild Speedmixer, Landrum S.C.). 1 g increments of water are added and mixed until a gel forms. 4-10 g increments of water are added and mixed to dilute the resultant emulsion. The final emulsion contains 24% copolymer. The particle size is measured using a Nicomp 370(Particle Sizing Systems, Santa Barbara, Calif.). The volume weighted median particle size is 135 nanometers.

k. 8175-GL-GTMAC Cationic Saccharide-Siloxane Emulsion W/Cationic Surfactant 50 g of a solution prepared according to Example 2j is placed on a rotary evaporator and the solvent removed until an 80% solid solution remains. 40 g of this solution, 2.5 g of 2-propanol, and 11.72 g of Arquad 16-29 cationic surfactant (Akzo Nobel, Amersfoort, the Netherlands) are placed in a disposable cup and mixed on a centrifugal mixer (Hauschild Speedmixer, Landrum S.C.). 2 g increments of water are added and mixed until a gel is formed. 4-5 g increments of water are added and mixed to dilute the resultant emulsion. The final emulsion contains 40% copolymer. The particle size is measured using a Nicomp 370(Particle Sizing Systems, Santa Barbara, Calif.). The volume-weighted median particle size is 211 nanometers.

l. A32-GL Saccharide-Siloxane Emulsion W/Cationic Surfactant 30 g of A32-GL sugar siloxane (described previously) is diluted with a 90/10 by weight solution of Isopar G (Exxon-Mobil Chemical) and 2-propanol until a 75% copolymer concentration is achieved. The dilution is accomplished by sequential additions of the solvent followed by mixing on a Hauschild Speedmixer™ centrifugal mixer (Flacktek, Inc. Landrum, S.C.) until homogenous. 1.6 g of Tergitol 15-S-3 (Dow Chemical Co., Midland, Mich.) is mixed into the saccharide-siloxane solution. 11.1 g of Arquad 16-29 (Akzo Nobel Surface Chemistry LLC, Chicago, Ill.) are then added and mixed until emulsified. Subsequent mixing is done until a clear gel forms. Additional water is added and mixed until a 50% internal phase concentration is achieved. The median volume particle size is 277 nm, measured with a Nicomp 370 (Particle Sizing Systems, Inc. Santa Barbara, Calif.).

m. A32-GL Sugar Siloxane Emulsion W/Nonionic Surfactant 25 g of A32-GL sugar siloxane (described previously) is diluted with a 90/10 by weight solution of Isopar G (Exxon-Mobil Chemical) and 2-propanol until a 75% copolymer concentration is achieved. The dilution is accomplished by sequential additions of the solvent followed by mixing on a Hauschild Speedmixer™ centrifugal mixer (Flacktek, Inc. Landrum, S.C.) until homogenous. 1 g of Tergitol 15-S-3 (Dow Chemical Co., Midland, Mich.) is mixed into the saccharide-siloxane solution. 3 g of Tergitol 15-S-40 (70%) (Dow Chemical Co., Midland, Mich.) and 3 g of deionized water are then added and mixed until emulsified. Subsequent mixing is done until a clear gel forms. Additional water is added and mixed until a 40% internal phase concentration is achieved. The median volume particle size is 537 nm, measured with a Nicomp 370 (Particle Sizing Systems, Inc. Santa Barbara, Calif.).

n. A32-LBL Sugar Siloxane Emulsion W/Nonionic Surfactant 2 g Tergitol 15-S-3 (Dow Chemical Co., Midland, Mich.) is mixed into 51 g of an A32-LBL saccharide-siloxane solution (44% saccharide-siloxane in 90/10 by weight Isopar G (ExxonMobil Chemical) and 2-propanol). 16.4 g of Tergitol 15-S-40 (70%) (Dow Chemical Co., Midland, Mich.) and 2.1 g of deionized water is then added and mixed until emulsified. Subsequent mixing continues until a clear gel forms. Additional water is added and mixed until a 45% internal phase concentration is achieved. The median volume particle size is 692 nm, measured with a Nicomp 370 (Particle Sizing Systems, Inc. Santa Barbara, Calif.).

TABLE 5

Saccharide-Siloxane Emulsion Characteristics

| Emulsion Containing Saccharide-Siloxane | Internal Phase Description | Internal Phase Concentration % | Saccharide-Siloxane Concentration % | Surfactant | Median Volume PS nm |
|---|---|---|---|---|---|
| 8175-GL GTMAC | 80% copolymer in IPA | 29.4 | 23.5 | 15-S-40 15-S-3 | 135 |
| A32-LBL | 44% copolymer in 90/10 Isopar G/IPA | 45.3 | 20.0 | 15-S-40 15-S-3 | 692 |
| A32-GL | 75% copolymer in 90/10 Isopar G/IPA | 40.0 | 30.0 | 15-S-40 15-S-3 | 537 |
| 8175-GL-GTMAC | 80% copolymer in IPA | 50.0 | 40.0 | Arquad 16-29 | 211 |
| A32-GL | 75% copolymer in 90/10 Isopar G/IPA | 50.0 | 37.5 | Arquad 16-29 15-S-3 | 277 |

Example 3

Personal Care Product Embodiment: Rinse-Off Conditioners

The following examples illustrate rinse-off conditioner compositions representative of the present invention, comprising saccharide-siloxane dispersion or emulsions, and results demonstrating their superior conditioning properties.

TABLE 6

Rinse-Off Conditioners Compositions by Weight %

| Ingredient | A | B | C | D | E |
|---|---|---|---|---|---|
| Deionized Water | q.s. to 100 | q.s. to 100 | q.s. to 100 | q.s. to 100 | q.s. to 100 |
| Hydroxyethylcellulose[1] | 1.5 | 1.5 | 1.5 | 1.5 | 1.5 |
| Cetearyl Alcohol[2] | 1 | 1 | 1 | 1 | 1 |
| PEG-100 Stearate & Glyceryl Stearate[3] | 1 | 1 | 1 | 1 | 1 |
| A12 LBL Saccharide-Siloxane[4] | 2 | | | | |
| A21-GL Saccharide-Siloxane[5] | | 2 | | | |
| A21-LBL Saccharide-Siloxane[6] | | | 2 | | |
| A32-GL Saccharide-siloxane[7] | | | | 2 | |
| 8175-GL Saccharide-Siloxane[8] | | | | | 2 |
| Cyclopentasiloxane[9] | 8 | 8 | 8 | 8 | 8 |
| DMDM Hydantoin[10] | 0.2 | 0.2 | 0.2 | 0.2 | 0.2 |

[1]Natrosol ® 250 HHR available from Hercules of Wilmington, DE
[2]Crodocol CS-50 ® available from Croda Inc. of Edison, NJ
[3]Arlacel ® 165 available from Uniqema of Wilmington, DE
[4]Concentration based on active silicone level, A = A12 LBL Dispersion (20% Active)
[5]Concentration based on active silicone level, B = A21-GL Dispersion (20% Active)
[6]Concentration based on active silicone level, C = A21-LBL Dispersion (20% Active)
[7]Concentration based on active silicone level, D = A32-GL Dispersion (20% Active)
[8]Concentration based on active silicone level, E = 8175-GL Dispersion (20% Active)
[9]Dow Corning ® 245 Fluid available from Dow Corning, Midland, MI
[10]Glydant ® available from Lonza, Inc. of Farilawn, NJ Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate & glyceryl stearate is added. Heat is then decreased to 40° C. and the silicone saccharide-siloxane dispersion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

TABLE 7

Rinse-Off Conditioner Compositions by Weight %

| Ingredient | F | G | H | I | J |
|---|---|---|---|---|---|
| Deionized Water | q.s. to 100 | q.s. to 100 | q.s. to 100 | q.s. to 100 | q.s. to 100 |
| Hydroxyethylcellulose[1] | 1.5 | 1.5 | 1.5 | 1.5 | 1.5 |
| Cetearyl Alcohol[2] | 1 | 1 | 1 | 1 | 1 |
| PEG-100 Stearate & Glyceryl Stearate[3] | 1 | 1 | 1 | 1 | 1 |
| 8175-GL Saccharide-Siloxane Emulsion[4] | 2 | | | | |
| 8175-GL GTMAC Saccharide-Siloxane Emulsion[5] | | 2 | | | |
| 32-GL Saccharide-Siloxane Emulsion[6] | | | 2 | | |
| 32-GL GTMAC Saccharide-Siloxane Emulsion[7] | | | | 2 | |
| 32 LBL Saccharide-Siloxane Emulsion[8] | | | | | 2 |
| Cyclopentasiloxane[9] | 8 | 8 | 8 | 8 | 8 |
| DMDM Hydantoin[10] | 0.2 | 0.2 | 0.2 | 0.2 | 0.2 |

[1]Natrosol ® 250 HHR available from Hercules of Wilmington, DE
[2]Crodocol CS-50 ® available from Croda Inc. of Edison, NJ
[3]Arlacel ® 165 available from Uniqema of Wilmington, DE
[4]Concentration based on active silicone level, F = 8175-GL Emulsion (23.5% Active)
[5]Concentration based on active silicone level, G = 8175-GL GTMAC Emulsion (40% Active)
[6]Concentration based on active silicone level, H = 32-GL Emulsion (30% Active)
[7]Concentration based on active silicone level, I = 32-GL GTMAC Emulsion (37.5% Active)
[8]Concentration based on active silicone level, J = 32 LBL Emulsion (20% Active)
[9]Dow Corning ® 245 Fluid available from Dow Corning, Midland, MI
[10]Glydant ® available from Lonza, Inc. of Farilawn, NJ Deionized water is added to the mixing vessel and heated to 75° C. In order to keep active silicone loading constant throughout testing, it is necessary to adjust the water level added depending on the percent active silicone in the various emulsions used. With moderate agitation, the hydroxyethyl cellulose is dispersed until fully dissolved. Heat is decreased to 60° C. and cetearyl alcohol and PEG-100 stearate & glyceryl stearate is added. Heat is then decreased to 40° C. and the saccharide-siloxane emulsion and cyclopentasiloxane is added to the base conditioner. The conditioner is mixed for 5-10 minutes and then DMDM hydantoin is added. The water loss is compensated for and the formulation is mixed for an additional 5 minutes. The final pH of all the conditioner formulations is approximately 6-7.

Slightly bleached European human hair from International Hair Importer and Products Inc. is used in a combing evaluation protocol for testing the conditioners. A master hand of hair about eight inches in length is subdivided into a series of individual hair tresses. Each tress weighed about 2.5 grams. A ½ inch of the root end of the hair was trimmed and glued to a 2"×2" plastic tab using DUCO CEMENT®. The cement is allowed to dry over night, and the hair tress is combed and trimmed to a length so that six inches of hair extends below the bottom of the plastic tab. A hole is punched in the middle of the tab about ¼" from the top. Each tress is rinsed for 15 seconds under 40° C. tap water. Using a pipette, 1.0 g of a 9% Sodium Lauryl Sulfate (active) solution is applied and lathered through the tress for 30 seconds. The tress is rinsed for 30 seconds under running water. Excess water is removed from the tress by passing the tress between the index and middle fingers. The tresses are placed on a tray covered with paper towels and dried overnight at ambient conditions. Each tress is hand-combed three times with the narrow teeth of an ACE® comb and evaluated using the INSTRON "WET" and the INSTRON "DRY" COMBING procedures.

For tests involving the rinse-off conditioner, the hair tress is rinsed with tap water for 30 seconds at 40° C. The test conditioner is applied to the tress in the amount of 0.8 g and the tress is stroked for 30 seconds. The tress is rinsed for 30 seconds under tap water at 40° C. The excess water is removed by pulling the tresses through the index and middle fingers. The tresses are allowed to dry separately on a paper towel, overnight at ambient conditions. The tresses are combed once before performing the Instron study.

INSTRON COMBING is an industry-recognized test for determining hair conditioning by the ease of wet combing and the ease of dry combing. The test employs an INSTRON strain gauge, which is equipped to measure the force required to comb the hair. Conditioning performance is based on the ability of a particular hair treatment formulation such as a shampoo or a hair conditioner to reduce the force required to comb the hair with the INSTRON strain gauge. The force is reported as Average Combing Load (ACL). The lower ACL value, the better the conditioning effect imparted by the formulation being tested. Typically, ACL baselines are initially established with "untreated" tresses that have only been washed with the sodium lauryl sulfate solution. The effectiveness of a treatment can be expressed as the ACL of the treated tress or the percent reduction in ACL which is calculated by the equation: [(ACL of untreated hair−ACL of treated hair)/ACL of untreated hair]×100.

According to the INSTRON WET COMBING method, the hair is first wetted by dipping in distilled water and then detangled by combing the tress three times. The tress is then retangled by dipping in distilled water three times. The excess water is removed by passing the tress through index and middle fingers twice. The tress is then placed on the hanger and INSTRON combed. The "retangle" and "Instron combing" steps are repeated until all data points are collected. An average combing force of three tresses is measured for each treatment. The result of the INSTRON WET COMBING test conducted with the conditioners of the present invention are shown below in Table 8. The results show that the conditioners comprising the saccharide-siloxanes provide a significant reduction in wet combing forces compared to the untreated tress, thereby demonstrating an improvement in the conditioning properties of the hair.

According to the INSTRON DRY COMBING method, hair is detangled by combing the tress three times. Then hair is retangled by swirling the tress clockwise three times and swirling it counter clockwise three times. The tress is then placed on a hanger and INSTRON combed. Retangle and Instron combing are repeated until all data points are collected. An average combing force for three tresses is measured for each treatment. The results show that the conditioners containing the saccharide-siloxanes provided a significant reduction in dry combing forces compared to the untreated tress, thereby improving the dry conditioning properties of the hair.

TABLE 8

INSTRON Combing Results for Conditioners Comprising Saccharide-Siloxane Dispersions

| Rinse Off Conditioner Containing Saccharide-Siloxane | Dry Combing | | | Wet Combing | | |
|---|---|---|---|---|---|---|
| | Avg Comb Load Untreated (kgf) | Avg Comb Load Treated (kgf) | Avg % Reduction | Avg Comb Load Untreated (kgf) | Avg Comb Load Treated (kgf) | Avg % Reduction |
| A12 LBL | 0.044 | 0.026 | 39.2% | 0.393 | 0.055 | 86.0% |
| A21 GL | 0.051 | 0.023 | 53.2% | 0.397 | 0.197 | 49.0% |
| A21 LBL | 0.049 | 0.041 | 15.6% | 0.381 | 0.307 | 16.5% |
| A32 GL | 0.044 | 0.015 | 66.8% | 0.453 | 0.138 | 68.9% |
| 8175 GL | 0.05 | 0.028 | 43.0% | 0.377 | 0.199 | 46.6% |

TABLE 9

INSTRON Combing Results for Conditioners Comprising Saccharide-Siloxane Emulsions

| Rinse Off Conditioner Containing Saccharide-Siloxane Emulsion | Dry Combing | | | Wet Combing | | |
|---|---|---|---|---|---|---|
| | Avg Comb Load Untreated (kgf) | Avg Comb Load Treated (kgf) | Avg % Reduction | Avg Comb Load Untreated (kgf) | Avg Comb Load Treated (kgf) | Avg % Reduction |
| 8175 GL-GTMAC Emulsion | 0.035 | 0.019 | 45.2% | 0.296 | 0.034 | 88.4% |
| 8175 GL-GTMAC Cationic Emulsion | 0.041 | 0.019 | 46.3% | 0.419 | 0.033 | 91.6% |
| 32 GL Emulsion | 0.040 | 0.020 | 49.9% | 0.374 | 0.106 | 71.8% |
| 32 GL Cationic Emulsion | 0.044 | 0.019 | 56.6% | 0.393 | 0.098 | 75.1% |
| 32 LBL Emulsion | 0.041 | 0.028 | 30.4% | 0.346 | 0.412 | −22.2% |

Example 4

Personal Care Product Embodiments: Shampoos

This example illustrates that conditioning shampoos comprising a saccharide-siloxane copolymer emulsion yield superior results when subject to the INSTRON COMBING evaluation method when compared to the control conditioning shampoo.

TABLE 10

Conditioning Shampoo Emulsion Compositions by Weight %

| Ingredient | A | B | C | D | E |
|---|---|---|---|---|---|
| Deionized Water | q.s. to 100 | q.s. to 100 | q.s. to 100 | q.s. to 100 | q.s. to 100 |
| Sodium Lauryl Ether Sulfate[1] | 30 | 30 | 30 | 30 | 30 |
| Cocamide DEA[2] | 3 | 3 | 3 | 3 | 3 |

TABLE 10-continued

Conditioning Shampoo Emulsion Compositions by Weight %

| Ingredient | A | B | C | D | E |
|---|---|---|---|---|---|
| Cocamidopropyl Betaine[3] | 7 | 7 | 7 | 7 | 7 |
| Polyquaternium-10[4] | 0.3 | 0.3 | 0.3 | 0.3 | 0.3 |
| PEG-150 Pentaerythrityl Testrastearate[5] | 1 | 1 | 1 | 1 | 1 |
| 8175-GL GTMAC Nonionic Emulsion[6] |  | 2 |  |  |  |
| 32-GL Nonionic Emulsion[7] |  |  | 2 |  |  |
| 32-LBL Nonionic Emulsion[8] |  |  |  | 2 |  |
| A32-LBL Emulsion[9] |  |  |  |  | 2 |
| DMDM Hydantoin[10] | 0.2 | 0.2 | 0.2 | 0.2 | 0.2 |

[1]Standapol ES-3 ® available from Cognix Corp. of Cincinnati, OH
[2]Monamid 705 ® available from Uniqema of New Castle, DE
[3]Monateric CAB-LC ® available from Uniqema of New Castle, DE
[4]UCARE Polymer JR-30M available from Dow/Amerchol of Midland, MI
[5]Crothix ® available from Croda Inc. of Edison, NJ
[6]Concentration based on active silicone level, B = 8175-GL GTMAC Nonionic Emulsion (40% Active)
[7]Concentration based on active silicone level, C = 32-GL Nonionic Emulsion (30% Active)
[8]Concentration based on active silicone level D = 32-LBL Nonionic Emulsion (37.5% Active)
[9]Concentration based on active silicone level, E = 32 LBL Emulsion (20% Active)
[10]Glydant ® available from Lonza, Inc. of Fairlawn, NJ Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, saccharide-siloxane emulsion is added to the base conditioner. The conditioner is mixed for 5-10 minutes and then DMDM hydantoin is added. The water loss is compensated for and the formulation is mixed for an additional 5 minutes. The final pH of the conditioner formulations is approximately 6-7.

Using the evaluation method for Instron Combing detailed above in the Rinse Off Conditioner Example, the conditioning shampoos are evaluated for wet and dry combing performance. An average combing force for three tresses is measured for each treatment. The results show that the shampoo containing the saccharide-siloxane provided a significant reduction in dry and wet combing forces compared to the control conditioning shampoo, thereby improving the dry and wet conditioning properties of the hair.

TABLE 11

Instron Combing Results - Conditioning Shampoo

| Conditioning Shampoo Containing Saccharide-Siloxane | Avg % Reduction Dry | Avg % Reduction Wet |
|---|---|---|
| Control Conditioning Shampoo | 11.6% | 36.9% |
| 8175 GL GTMAC Nonionic Emulsion | 34.5% | 60.8% |
| 32 GL Nonionic Emulsion | 49.8% | 44.3% |
| 32 GL Cationic Emulsion | 53.3% | 67.4% |
| 32 LBL Emulsion | 61.3% | 68.1% |

Example 5

Personal Care Product Embodiments: Clear Hair Serums

This example illustrates that Clear Hair Serums comprising Saccharide-Siloxane solutions exhibit superior shine and higher viscosity when compared to Clear Hair Serums without the saccharide-siloxane ingredient.

TABLE 12

Clear Hair Serum Compositions by Weight %

| Ingredient | A | B | C |
|---|---|---|---|
| Cyclopentasiloxane[1] | 50 | 50 | 50 |
| Cyclopentasiloxane & Dimethiconol[2] | 46.4 | 46.4 | 46.4 |
| Amodimethicone[3] | 3.6 |  |  |
| A32-GL[4] |  | 3.6 |  |
| A32-LBL[5] |  |  | 3.6 |

[1]Dow Corning ® 245 Fluid available from Dow Corning, Midland, MI
[2]Dow Corning ® 1501 Fluid available from Dow Corning, Midland, MI
[3]Dow Corning ® 2-8566 Amino Fluid available from Dow Corning, Midland, MI
[4]Concentration based on active silicone level, C = A32-GL Dispersion (20% Active)
[5]Concentration based on active silicone level, D = A32-LBL Dispersion (20% Active)

TABLE 13

Paired Comparison ASTM protocol E1958-98 Results

| | Paired Comparison # | | |
|---|---|---|---|
| | 1 | 2 | 3 |
| Compositions Compared | A:B | A:C | B:C |
| Shine Result | 10:6 | 2:14* | 0:16** |

Saccharide-siloxane solid is dissolved in cyclopentasiloxane by heating the mixture to 70° C. and mixing periodically until completely dispersed. The dispersion is then cooled to 50° C. before adding cyclopentasiloxane & dimethiconol &/or amodimethicone Fluid and mixed until serum reaches room temperature.

Sensory testing for shine attributes is performed on formulations paired as A vs. B, A vs. C, and B vs. C according to ASTM Standards E 1958-98 (Standard Guide for Sensory Claim Substantiation) and E 253 (Terminology Relating to Sensory Evaluation of Materials and Products), and ISO Standard 6658 (Sensory Analysis-Methodology-General Guidance). The results are reported in Table 13. A product with an asterisk next to it means that there is a statistical difference at the 95% confidence level. A product with a double asterisk next to it means that there is a statistical difference at the 99% confidence level.

Example 6

Personal Care Product Embodiments: Soft Solid Antiperspirants

This example illustrates the formulation of a soft-solid antiperspirant comprising a saccharide-siloxane copolymer ingredient. The saccharide-siloxane solution provides thickening sufficient to maintain suspension of the antiperspirant salt without use of additional thickener.

TABLE 14

Antiperspirant Soft Solid Composition

| Ingredient | Composition Weight % |
|---|---|
| Hydrogenated Castor Oil[1] | 1.0 |
| Aluminum Zirconium Tetrachlorohydrex GLY[2] | 50.0 |
| Dimethicone[3] | 15.0 |
| Cyclopentasiloxane[4] | 54.0 |
| Stearyl Dimethicone[5] | 1.0 |
| Saccharide-Siloxane[6] | 4.0 |

[1]Cutina HR ® available from Cognis Corp., Hoboken, NJ
[2]AZG-370 ® available from Summit Research Labs, Flemington, NJ
[3]Dow Corning ® 200 Fluid, 10 cst available from Dow Corning, Midland, MI
[4]Dow Corning ® 245 Fluid available from Dow Corning, Midland, MI
[5]Dow Corning ® 2503 Wax available from Dow Corning, Midland, MI
[6]Concentration based on active silicone level, A32-GL Dispersion (20% Active)

Dimethicone is heated to 50° C. Hydrogenated castor oil and stearyl dimethicone are added and mixed until melted and homogenous. The mixture is cooled to below 40° C. and cyclopentasiloxane and the saccharide-siloxane are added while continuing to mix. The aluminum zirconium tetrachlorohydrex is slowly added and mixing continues until the powder is fully dispersed.

The benefit of being able to formulate with reduced or no additional thickener (i.e. hydrogenated castor oil in this example) is realized as the saccharide-siloxane dispersion provides sufficient thickening to maintain suspension of the AP salt. This example uses 1% of the hydrogenated castor oil thickening agent vs. typical levels of 2-6% depending on the AP salt active.

Example 7

Personal Care Product Embodiments: Antiperspirant Gels

This example illustrates preparation of a gel antiperspirant composition. Incorporation of either a A21-GL or A32-GL solution results in a particularly stable AP gel formulation which exhibits thickening benefits. Inclusion of A32-GL reduces the amount of cyclopentasiloxane & PEG/PPG-18/18 dimethicone needed from the amount found in a standard formulation, while the AP gel retains properties such as decreased slip and increased thickness. A32-GL also decreases whitening versus control group formulations.

TABLE 15

Antiperspirant Gel Compositions by Weight %

| Ingredient | A | B | C |
|---|---|---|---|
| Deionized Water | q.s. to 100 | q.s. to 100 | q.s. to 100 |
| Aluminum Sequichlorohydrate[1] | 50 | 50 | 50 |
| Propylene Glycol[2] | 10 | 10 | 10 |
| Cyclopentasiloxane[3] | 8 | 8 | 8 |
| Cyclopentasiloxane & PEG/PPG-18/18 Dimethicone[4] | 6 | 2 | 2 |
| A21-GL[5] | | 2 | |
| A32-GL[6] | | | 2 |

[1]Reach 301 ® available from Reheis, Inc., Berkeley Heights, NJ
[2]Propylene Glycol available from Fisher Scientific, Fair Lawn, NJ
[3]Dow Corning ® 245 Fluid available from Dow Corning, Midland, MI
[4]Dow Corning ® 5225C Formulation Aid available from Dow Corning, Midland, MI
[5]Concentration based on active silicone level, B = A21-GL Dispersion (20% Active)
[6]Concentration based on active silicone level, C = A32-GL Dispersion (20% Active)

The propylene glycol, cyclopentasiloxane, sugar siloxane and cyclopentasiloxane & PEG/PPG-18/18 dimethicone (Phase A) ingredients are mixed in beaker until homogeneous. Aluminum sequichlorohydrate and water (Phase B) are separately pre-mixed. Phase B is slowly added to Phase A with high agitation.

The A21 and A32 saccharide-siloxanes were capable of forming stable AP gel formulations, with increased thickening benefits. The A32 saccharide-siloxane also demonstrates emulsification properties, since lower levels of the formulation aid cyclopentasiloxane & PEG/PPG-18/18 dimethicone are needed than in a standard AP formulation. The AP formulated with the A32 saccharide-siloxane exhibited nice skin feel properties in addition to increased thickening benefits. In addition, there is less white residue left on the skin after application and drying of the formulation comprising the A32 saccharide-siloxane when compared to the control formulation without the saccharide-siloxane.

Example 8

Personal Care Product Embodiments: Facial Lotions

This example illustrates the beneficial characteristic profile of a facial lotion composition comprising a saccharide-siloxane copolymer ingredient.

TABLE 16

Facial Lotion Compositions by Weight %

| Ingredient | A | B |
|---|---|---|
| Deionized Water | q.s. to 100 | q.s. to 100 |
| Glycerin[1] | 4.2 | 4.2 |
| Polyacrylamide & C13-14 Isoparaffin & Laureth-7[2] | 3.2 | 3.2 |
| Cyclopentasiloxane[3] | 5.5 | 5.5 |
| DMDM Hydantoin[4] | 1 | 1 |
| Cyclopentasiloxane & Dimethicone Crosspolymer[5] | 0.8 | |
| A32-LBL[6] | | 0.8 |

[1]Glycerin available from Fisher Scientific, Fair Lawn; NJ
[2]Sepigel 305 ® available from Seppic, Paris, FR
[3]Dow Corning ® 245 Fluid available from Dow Corning, Midland, MI
[4]Glydant ® available from Lonza, Inc. of Fairlawn, NJ
[5]Dow Corning ® 9045 Elastomer Blend available form Dow Corning, Midland, MI; Concentration based on active silicone level A = Control (12.5% Active)
[6]Concentration based on active silicone level, B = A32-LBL Dispersion (20% Active)

Water, glycerin, cyclopentasiloxane, saccharide-siloxane & DMDM hydantoin are mixed for 5-10 minutes or until the mixture is homogeneous. Polyacrylamide, C13-14 isoparaffin and laureth-7 are added to the mixture. As the material thickens, mixing speed is increased. Mixing continues at high speeds for an additional 5-10 minutes or until the material attains a smooth consistency.

Sensory testing for skin feel attributes is performed on formulations A and B according to ASTM Standards E 1958-98 (Standard Guide for Sensory Claim Substantiation) and E253 (Terminology Relating to Sensory Evaluation of Materials and Products), and ISO Standard 6658 (Sensory Analysis, Methodology, General Guidance). The comparative results are depicted in Table 17.

The results for the formulation comprising the saccharide-siloxane are statistically similar to the results for formulations comprising a silicone elastomer with respect to the attributes of absorption, tack, smoothness and gloss. However, the saccharide-siloxane formulations are thicker to a statistically significant extent.

TABLE 17

Comparative Benefits Profile for Facial Lotion Compositions

| Composition | A | B |
|---|---|---|
| Absorption (fewer rubs) | 10 | 6 |
| Thickness | 3 | 13* |
| Tack | 8 | 8 |
| Smoothness | 10 | 6 |

*= significant difference with alpha <0.05

Example 9

Personal Care Product Embodiments: Cosmetic Liquid Foundations

This example illustrates a liquid foundation composition comprising a saccharide-siloxane copolymer ingredient. This formulation exhibits an unusual consistency. It is very high in viscosity (almost solid), yet seems to "melt" when rubbed making it easy to apply to the skin.

TABLE 18

Liquid Foundation Composition by Weight %

| Ingredient | |
|---|---|
| Deionized Water | q.s. to 100 |
| Cyclopentasiloxane & PEG/PPG-18/18 Dimethicone[1] | 7.5 |
| Cyclopentasiloxane[2] | 21.1 |
| Dimethicone[3] | 9.4 |
| Titanium Dioxide[4] | 4.7 |
| Iron Oxide (yellow)[5] | 0.2 |
| Iron Oxide (red)[6] | 0.2 |
| Iron Oxide (black)[7] | 0.2 |
| Diazolidinyl Urea & Iodopropynyl Butylcarbamate[8] | 0.3 |
| Propylene Glycol[9] | 8.0 |
| Sodium Chloride[10] | 1.0 |
| Laureth-7[11] | 0.1 |
| Saccharide-siloxane[12] | 1.6 |

[1]Dow Corning ® 5225C Process Aid available from Dow Corning, Midland, MI
[2]Dow Corning ® 245 Fluid available fromDow Corning, Midland, MI
[3]Dow Corning ® 200 Fluid, 5 cst available from Dow Corning, Midland, MI
[4]Cardre Titanium Dioxide available from Cardre, Inc., South Plainfield, NJ
[5]Cardre Yellow Iron Oxide AS available from Cardre, Inc., South Plainfield, NJ
[6]Cardre Red Iron Oxide AS available from Cardre, Inc., South Plainfield, NJ
[7]Cardre Black Iron Oxide AS available from Cardre, Inc., South Plainfield, NJ
[8]Germall Plus available from Sutton Laboratories, Chatham, NJ
[9]Propylene Glycol available from Fisher Scientific, Fair Lawn, NJ
[10]Sodium Chloride available from Fisher Scientific, Fair Lawn, NJ
[11]Rhodasurf L-7 90 available from Rhodia Inc., Cranbury, NJ
[12]Concentration based on active silicone level A32-LBL Dispersion (20% Active)

A32-LBL saccharide-siloxane material is dispersed in cyclopentasiloxane by heating the mixture to 70° C. and mixing periodically. Cyclopentasiloxane and PEG/PPG 18/18 dimethicone, dimethicone, titanium dioxide and iron oxides are added in sequential order to the dispersion with continued heating. This mixture is kept at 70° C. and mixed at moderate speeds until all pigments are dispersed and the material achieves a smooth consistency (10-20 minutes). Water, diazolidinyl urea & iodopropyiiyl butylcarbamate, propylene glycol, sodium chloride and laureth-7 are combined in a separate beaker. This mixture is slowly added to the initial phase using high shear (1300-1400 rpm) techniques until completely incorporated. Viscosity for foundation comprising the saccharide-siloxane material is 19,800 cP verses 2,700 cP for a control foundation without the sugar siloxane.

Example 10

Personal Care Product Embodiments: Cosmetic Liquid Foundations Using Crosslinked Saccharide Siloxane This example illustrates a cosmetic formulation comprising crosslinked saccharide-siloxane copolymers. Benefits of the cross-linked saccharide siloxane in cosmetic formulations include desirable sensory attributes and thickening. Other potential benefits include film forming, substantivity, durability and wash-off resistance.

TABLE 19

Liquid Foundation Composition by Weight Percent

| Ingredient | |
|---|---|
| Deionized Water | q.s. to 100 |
| Cyclopentasiloxane & PEG/PPG-18/18 Dimethicone[1] | 7.5 |
| Cyclopentasiloxane[2] | 25.4 |
| Dimethicone[3] | 4.4 |
| Titanium Dioxide[4] | 4.7 |
| Iron Oxide (yellow)[5] | 0.2 |
| Iron Oxide (red)[6] | 0.3 |
| Iron Oxide (black)[7] | 0.1 |
| Diazolidinyl Urea & Iodopropynyl Butylcarbamate[8] | 0.3 |
| Propylene Glycol[9] | 8.0 |
| Sodium Chloride[10] | 1.0 |
| Laureth-7[11] | 0.1 |
| Saccharide-siloxane[12] | 1.6 |
| Triisopropanolamine borate[13] | 0.07 |

[1]Dow Corning ® 5225C Process Aid available from Dow Corning, Midland, MI
[2]Dow Corning ® 245 Fluid available from Dow Corning, Midland, MI
[3]Dow Corning ® 200 Fluid, 5 cst available from Dow Corning, Midland, MI
[4]Cardre Titanium Dioxide available from Cardre, Inc., South Plainfield, NJ
[5]Cardre Yellow Iron Oxide AS available from Cardre, Inc., South Plainfield, NJ
[6]Cardre Red Iron Oxide AS available from Cardre, Inc., South Plainfield, NJ
[7]Cardre Black Iron Oxide AS available from Cardre, Inc., South Plainfield, NJ
[8]Germall Plus available from Sutton Laboratories, Chatham, NJ
[9]Propylene Glycol available from Fisher Scientific, Fair Lawn, NJ
[10]Sodium Chloride available from Fisher Scientific, Fair Lawn, NJ
[11]Rhodasurf L-7 90 available from Rhodia Inc., Cranbury, NJ
[12]Concentration based on active silicone level A32-LBL Dispersion (20% Active)
[13]Triisopropanolamine Borate available Anderson Development Co., Adrian, MI A32-LBL saccharide-siloxane dispersion is dispersed in cyclopentasiloxane by heating the mixture to 70° C. and mixing periodically. Titanium dioxide and iron oxides are added to a portion of the cyclopentasiloxane independently at high shear to disperse the powers into a materbatch. Cyclopentasiloxane/pigment dispersion and PEG/PPG 18/18 dimethicone and dimethicone are added in sequential order to the saccharide-siloxane dispersion with continued heating. This mixture is kept at 70° C. and mixed at moderate speeds until all pigments are dispersed and the material achieves a smooth consistency (10-20 minutes). Water, diazolidinyl urea and iodopropynyl butylcarbamate, propylene glycol, sodium chloride, laureth-7 and triisopropanolamine borate are combined in a separate beaker. This mixture is slowly added to the initial phase using high shear (1300-1400 rpm) until completely incorporated. Final foundation showed similar shear thickening behavior as the non-crosslinked formulation in Example 9.

Example 11

Personal Care Product Embodiments: Liquid Hair Gels

This example illustrates several liquid hair gel formulations comprising saccharide-siloxane copolymers.

TABLE 20

Liquid Hair Gel Compositions by Weight %

| Ingredient | A | B | C | D | E |
|---|---|---|---|---|---|
| Deionized Water | q.s. to 100 | q.s. to 100 | q.s. to 100 | q.s. to 100 | q.s. to 100 |
| Acrylates/C10-30 alkyl Acrylate Crosspolymer[1] | 1 | 1 | 1 | 1 | 1 |
| Triethanolamine[2] | 0.06 | 0.06 | 0.06 | 0.06 | 0.06 |
| PVP/VA Copolymer[3] | 4.5 | 4.5 | 4.5 | 4.5 | 4.5 |
| A12 LBL[4] | | 2 | | | |
| A21-GL[5] | | | 2 | | |
| A32-GL[6] | | | | 2 | |
| 8175-GL[7] | | | | | 2 |
| DMDM Hydantoin[8] | 0.3 | 0.3 | 0.3 | 0.3 | 0.3 |

[1]Carbopol ETD2020 available form Noveon Inc., of Cleveland, OH
[2]Triethanolamine Care available form BASF of Ledgewood, NJ
[3]Luviskol VA 64 available form BASF of Ledgewood, NJ
[4]Concentration based on active silicone level, B = 12-GL Dispersion (20% Active)
[5]Concentration based on active silicone level, C = 21-GL Dispersion (20% Active)
[6]Concentration based on active silicone level, D = 32-GL Dispersion (20% Active)
[7]Concentration based on active silicone level, E = 8175-GL Dispersion (20% Active)
[8]Glydant ® available from Lonza, Inc. of Fairlawn, NJ Deionized water is added to a mixing vessel. Acrylates/C10-C30 alkyl acrylate crosspolymer and PVP/VA copolymer are added while mixing and mixing continues until fully dispersed. The gel solution is neutralized with triethanolamine. Saccharide-siloxane copolymer dispersions are added and mixing continues until homogeneous. DMDM hydantoin is added and mixing continues for an additional 10 minutes. The final pH of the fixative formulations is adjusted to approximately 6-7.

Example 12

Personal Care Product Embodiments: Liquid Hair Gels Using Crosslinked Saccharide Siloxane

TABLE 21

Liquid Hair Gel Compositions by Weight %

| Ingredient | Saccharide Siloxane | Control | PVP/VA |
|---|---|---|---|
| Deionized Water | q.s. to 100 | q.s. to 100 | q.s. to 100 |
| Acrylates/C10-30 alkyl Acrylate Crosspolymer (2%)[1] | 25% | 25% | 25% |
| Triethanolamine[2] | q.s. to neutralize | q.s. to neutralize | q.s. to neutralize |
| PEG-60 Hydrogenated Castor Oil[3] | 1.0 | 1.0 | 1.0 |
| Saccharide-siloxane[4] | 4.0 | | |
| Triisopropanolamine borate[5] | 0.07 | | |
| PVP/VA Copolymer[6] | | | 4.0 |
| DMDM Hydantoin[7] | 0.4 | 0.4 | 0.4 |

[1]Carbopol ETD2020 available form Noveon Inc., of Cleveland, OH
[2]Triethanolamine Care available form BASF of Ledgewood, NJ
[3]Cremophor CO 60 available from BASF of Mount Olive, NJ
[4]Concentration based on active silicone level, D = 32-GL Dispersion (20% Active)
[5]Triisopropanolamine Borate available Anderson Development Co., Adrian, MI
[6]Luviskol VA 64 available form BASF of Ledgewood, NJ
[7]Glydant ® available from Lonza, Inc. of Fairlawn, NJ Deionized water and triisopropanolamine borate are added to a mixing vessel. Acrylates/C10-C30 alkyl acrylate crosspolymer is added while mixing and mixing continues until fully dispersed. PEG-60 Hydrogenated Castor Oil and Saccharide-siloxane copolymer dispersion are added and mixed until homogeneous. DMDM hydantoin is added and mixing continues for an additional 10 minutes. The final pH of the fixative formulations is adjusted to approximately 6-7.

Benefits of the crosslinked saccharide siloxane in hair care formulations include conditioning, curl retention and styling benefits. Other benefits may include thickening, film forming, substantivity and durability.

Example 13

Personal Care Product Embodiments: Curl Retention Benefits

This example illustrates that hair-directed personal care products formulated from the personal care compositions comprising a saccharide-siloxane copolymer exhibit enhanced hair styling benefits as measured by curl retention. "Curl retention" is an industry-recognized test for determining hair styling and hold properties. The test involves subjecting curled hair tresses to constant temperature and humidity conditions for a specified period of time. Curl retention is then measured by recording the difference in length of curled hair tresses before and during high humidity and constant temperature conditions.

Already prepared natural virgin brown round hair tresses weighing 2 grams and measuring 25 cm long are secured. The tresses are pre-treated by applying and lathering a 1.0 gram solution containing nine percent sodium lauryl sulfate through each tress for 30 seconds. Each tress is then rinsed for 30 seconds under running water. Excess water is removed from each tress by passing the tress between the index and middle fingers of the hand. The tresses are placed on a tray covered with paper towels and dried overnight. Each tress is hand combed three times with the narrow teeth of a comb. Each tress is then wetted for 15 seconds under tap water at 37° C. and the excess water is removed by pulling the tress through the index and middle fingers of the hand. Each of the tresses is then treated with either 500 microliters of a 6% active saccharide-siloxane emulsion, 6% dispersion diluted in cyclopentasiloxane, a 2% active silicone hair gel formulation (see Example 10 for composition), or rinse off conditioner formulation (see Example 3 for composition). Each tress is curled around a ¼" spiral perm rod and dried in a 40° C. oven overnight. The tresses are removed from the rod, keeping the curl intact and hung in a humidity chamber. The conditions of the humidity chamber are 25° C. and 70% relative humidity. The tress lengths are then measured periodically over 5 hours. Following the test, the maximum tress length is measured by unrolling it completely. The percent curl retention is calculated using the relationship:

(maximum tress length−tress length at specific time)/(maximum tress length−tress length at time=0)×100

An average of two tresses are measured for each treatment. The curl retention, expressed as a percentage, is recorded after 5 hours and the results demonstrate a statistical difference between the diluted saccharide siloxanes and both the deionized water and cyclopentasiloxane standards. Sensory feel and visual observations are also noted after the curl retention testing is completed.

TABLE 22

Curl Retention - Saccharide-Siloxane Dispersion 6% Active Dilutions

| Dilution Containing Saccharide-Siloxane | Curl Retention (%) after 5 hrs | Observations |
| --- | --- | --- |
| Deionized Water (DIW) | 29.6 | Difficult to comb, no spring back |
| A21-GL | 52.6 | Waxy feel, easy to comb, slight spring back |
| A32-GL | 54.2 | Soft, easy to comb, some spring back |
| A21-LBL | 58.4 | Difficult to comb, slightly coated feel, some spring back |
| A32-LBL | 50.6 | Nice feel, easy to comb, good spring back |
| DC 245 Fluid | 31.8 | Difficult to comb, no spring back |

TABLE 23

Curl Retention - Saccharide-Siloxane Emulsion 6% Active Dilution

| Dilution Containing Saccharide-Siloxane | Cure Retention (%) after 5 hrs | Observations |
| --- | --- | --- |
| Deionized Water (DIW) | 31.8 | Difficult to comb, no spring back |
| A32 GL Emulsion | 40.0 | Well defined curl, soft smooth feel with good springback, easy to comb with no residue |
| A32 GL Cationic Emulsion | 38.1 | Easy to comb, good feel, some spring back |
| 8175 GL Emulsion | 47.8 | More difficult to comb, slightly coated waxy feel, slight bounce back |
| 8175 GL Cationic Emulsion | 45.4 | Easy to comb, slightly coated feel, no bounce |

TABLE 24

Curl Retention - Saccharide-Siloxane Emulsion Hair Gel Formulation

| Dilution Containing Saccharide-Siloxane Emulsion | Curl Retention (%) after 5 hrs | Observations |
| --- | --- | --- |
| Deionized Water (DIW) | 23.8 | Difficult to comb, no spring back |
| A32-GL Emulsion | 33.7 | Well defined, soft smooth feel with good spring back, easy to comb |
| A32-GL GTMAC Emulsion | 32.9 | Easy to comb, good feel, some spring back |
| 8175-GL Emulsion | 32.0 | More difficult to comb, not as soft as A32-GL, some spring back |
| 8175-GL GTMAC Emulsion | 32.1 | Difficult to comb, not as soft as A32-GL, some spring back |
| PVP/VA | 32.9 | Curl ends not as defined as other samples, crispy feel, not as much spring back |

TABLE 25

Curl Retention - Saccharide-Siloxane Rinse Off Conditioner

| Rinse Off Conditioner Containing Saccharide-Siloxane | Curl Retention (%) after 5 hrs | Observations |
|---|---|---|
| Deionized Water (DIW) | 29.7 | Difficult to comb, no spring back |
| A32-GL Rinse Off Conditioner | 37.2 | Easy to comb, soft feel, some spring back |

TABLE 26

Curl Retention - Crosslinked Saccharide-Siloxane Dispersion Hair Gel Formulation

| Formulation | Curl Retention (%) after 5 hrs | Observations |
|---|---|---|
| Deionized Water (DIW) | 26.9 | Difficult to comb, minimum spring back |
| Control | 26.7 | Difficult to comb, some spring back |
| Crosslinked A32-GL | 38.0 | Easy to comb, very good spring back, smooth feel |
| PVP/VA | 29.6 | Difficult to comb, some spring back, tacky feel |

The invention claimed is:

1. A cosmetic composition comprising a carrier suitable to permit topically application of the cosmetic composition, and at least one saccharide-siloxane copolymer having a saccharide component, an organosiloxane component and a linking group, wherein the saccharide-siloxane copolymer has the following formula:

$$R^2_a R^1_{(3-a)}\text{—SiO—}[(SiR^2R^1O)_m\text{—}(SiR^1_2O)_n]_y\text{—}SiR^1_{(3-a)}R^2_a$$

wherein each $R^1$ can be the same or different and comprises hydrogen, $C_1$-$C_{12}$ alkyl, an organic radical, or $R^3$-Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each a is independently 0, 1, 2, or 3, y is an integer such that the copolymer has a molecular weight less than 1 million, $R^2$ has the formula $Z\text{-}(G^1)_b\text{-}(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:
$R^3\text{—NHC(O)O—}R^4\text{—}$;
$R^3\text{—NH—C(O)—NH—}R^4\text{—}$;
$R^3\text{—CH(OH)—CH}_2\text{—O—}R^4\text{—}$;
$R^3\text{—S—}R^4$
$R^3\text{—CH(OH)—CH}_2\text{—NH—}R^4\text{—}$; and
$R^3\text{—N(R}^1\text{)—}R^4$, and $R^3$ and $R^4$ are divalent spacer groups comprising $(R^5)_r(R^6)_s(R^7)_t$, wherein at least one of r, s and t must be 1, and $R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^{9o}$ may be the same or different, $R^6$ is $\text{—N(R}^8\text{)—}$, where $R^8$ is H or $C_1$-$C_{12}$ alkyl, or is Z—X wherein Z is previously defined or $R^3$, and X is a carboxylic acid, phosphate, sulfate, sulfonate or quaternary ammonium radical, and at least one of $R^3$ and $R^4$ must be present in the linking group and may be the same or different.

2. The cosmetic composition of claim 1 wherein the linking group comprises an amino, a urethane, a urea, a thioether, or an acetyl functional linking group.

3. The cosmetic composition of claim 1 wherein the linking group comprises an amino functional linking group.

4. The cosmetic composition of claim 1 wherein the at least one saccharide-siloxane copolymer is cross-linked.

5. The cosmetic composition of claim 1 wherein $G^2$ is a saccharide component comprising 5 to 12 carbons.

6. The cosmetic composition of claim 1 wherein the cosmetic composition is a facial foundation.

7. The cosmetic composition of claim 1 wherein the cosmetic composition is a cover up.

8. The cosmetic composition of claim 1 wherein the cosmetic composition is an emulsion.

9. The cosmetic composition of claim 1 wherein the cosmetic composition is a lotion or a cream.

10. The cosmetic composition of claim 1 further including a fragrance.

11. The cosmetic composition of claim 1 wherein the cosmetic composition includes 0.2 to 10% saccharide-siloxane by weight percent.

12. A skin-care composition comprising a carrier suitable to permit topically application of the skin-care composition, and at least one saccharide-siloxane copolymer having a saccharide component, an organosiloxane component and a linking group, wherein the saccharide-siloxane copolymer has the following formula:

$$R^2_a R^1_{(3-a)}\text{—SiO—}[(SiR^2R^1O)_m\text{—}(SiR^1_2O)_n]_y\text{—}SiR^1_{(3-a)}R^2_a$$

wherein each $R^1$ can be the same or different and comprises hydrogen, $C_1$-$C_{12}$ alkyl, an organic radical, or $R^3$—Q, Q comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each a is independently 0, 1, 2, or 3, y is an integer such that the copolymer has a molecular weight less than 1 million, $R^2$ has the formula $Z\text{-}(G^1)_b\text{-}(G^2)_c$, and there is at least one $R^2$ per copolymer, wherein $G^1$ is a saccharide component comprising 5 to 12 carbons, b+c is 1-10, b or c can be 0, $G^2$ is a saccharide component comprising 5 to 12 carbons additionally substituted with organic or organosilicon radicals, Z is the linking group and is independently selected from the group consisting of:
$R^3\text{—NHC(O)O—}R^4\text{—}$;

$R^3$—NH—C(O)—NH—$R^4$—;
$R^3$—CH(OH)—CH$_2$—O—$R^4$—;
$R^3$—S—$R^4$
$R^3$—CH(OH)—CH$_2$—NH—$R^4$—; and
$R^3$—N($R^1$)—$R^4$, and $R^3$ and $R^4$ are divalent spacer groups comprising $(R^5)_r(R^6)_s(R^7)_t$, wherein at least one of r, s and t must be 1, and $R^5$ and $R^7$ are independently an alkylene group of 1 to 12 carbons or a group of formula $(R^9O)_p$ wherein p is any integer 1-50, each $R^9$ is a divalent organic group of 1 to 12 carbons and each $R^{90}$ may be the same or different, $R^6$ is —N($R^8$)—, where $R^8$ is H or $C_1$-$C_{12}$ alkyl, or is Z—X wherein Z is previously defined or $R^3$, and X is a carboxylic acid, phosphate, sulfate, sulfonate or quaternary ammonium radical, and at least one of $R^3$ and $R^4$ must be present in the linking group and may be the same or different, wherein the skin-care composition provides a, therapeutic or protective benefit after being topically applied.

13. The skin-care composition of claim 12 wherein the linking group comprises an amino, a urethane, a urea, a thioether, or an acetyl functional linking group.

14. The skin-care composition of claim 12 wherein the linking group comprises an amino functional linking group.

15. The skin-care composition of claim 12 wherein the at least one saccharide-siloxane copolymer is cross-linked.

16. The skin-care composition of claim 12 wherein $G^2$ is a saccharide component comprising 5 to 12 carbons.

17. The skin-care composition of claim 12 further including a moisturizer.

18. The skin-care composition of claim 12 further including an antiperspirant agent.

19. The skin-care composition of claim 12 further including a deodorant agent.

20. The skin-care composition of claim 12 further including a sunscreen agent.

21. The skin-care composition of claim 12 further including an acne remover.

22. The skin-care composition of claim 12 further including a wrinkle remover.

23. The skin-care composition of claim 12 wherein the cosmetic composition is a lotion, cream or ointment.

24. The skin-care composition of claim 12 wherein the cosmetic composition provides a therapeutic benefit.

25. The skin-care composition of claim 12 wherein the cosmetic composition provides a protective benefit.

26. The skin-care composition of claim 12 wherein the cosmetic composition includes 0.2 to 10% saccharide-siloxane by weight percent.

27. A method of applying a cosmetic composition, the method comprising:
providing a cosmetic composition including a carrier suitable to permit topically application of the cosmetic composition according to claim 1; and
topically applying the cosmetic composition onto the skin.

28. A method of applying a skin-care composition, the method comprising:
providing a skin-care composition including a carrier suitable to permit topically application of the skin-care composition according to claim 12; and
topically applying the skin-care composition onto the skin.

* * * * *